United States Patent
Moradi et al.

(10) Patent No.: US 10,414,730 B2
(45) Date of Patent: Sep. 17, 2019

(54) CATALYTIC HYDROGENATION OF NITRILES

(71) Applicant: BAYER CROPSCIENCE AKTIENGESELLSCHAFT, Monheim am Rhein (DE)

(72) Inventors: Wahed Ahmed Moradi, Monheim (DE); Thomas Himmler, Odenthal (DE); Thomas Norbert Müller, Wehr (DE); Albert Schnatterer, Leverkusen (DE); Günter Schlegel, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/969,633

(22) Filed: May 2, 2018

(65) Prior Publication Data
US 2018/0244621 A1 Aug. 30, 2018

Related U.S. Application Data

(62) Division of application No. 15/033,987, filed as application No. PCT/EP2014/074212 on Nov. 11, 2014, now Pat. No. 9,988,353.

(30) Foreign Application Priority Data

Nov. 15, 2013 (EP) .................................... 13193164

(51) Int. Cl.
| C07D 213/56 | (2006.01) |
| C07D 213/89 | (2006.01) |
| C07D 213/38 | (2006.01) |
| C07D 213/57 | (2006.01) |

(52) U.S. Cl.
CPC ......... *C07D 213/56* (2013.01); *C07D 213/38* (2013.01); *C07D 213/57* (2013.01); *C07D 213/89* (2013.01)

(58) Field of Classification Search
CPC .................................................. C07D 513/56
See application file for complete search history.

(56) References Cited

U.S. PATENT DOCUMENTS

| 7,572,818 B2 | 8/2009 | Mansfield et al. |
| 7,777,045 B2 | 8/2010 | Lhermitte et al. |
| 2008/0114176 A1 | 5/2008 | Lhermitte et al. |
| 2013/0079554 A1 | 3/2013 | Yang et al. |

FOREIGN PATENT DOCUMENTS

| CN | 101080390 A | 11/2007 |
| EP | 1674455 A1 | 6/2006 |
| JP | 07138209 A | 5/1995 |
| WO | 9741846 A1 | 11/1997 |
| WO | 03070727 A1 | 8/2003 |
| WO | 2004016088 A2 | 2/2004 |
| WO | 2004041210 A2 | 5/2004 |
| WO | 2008125839 A2 | 10/2008 |
| WO | 2011047156 A1 | 4/2011 |

OTHER PUBLICATIONS

Nishimura, "Handbook of Heterogeneous Catalytic Hydrogenation for Organic Synthesis", pp. 254-285, John Wiley and Sons, New York, 2001.
Nishimura, "Handbook of Heterogeneous Catalytic Hydrogenation for Organic Synthesis", pp. 623-637, John Wiley and Sons, New York, 2001.
Skerlj, Remato T. et al., "Palladium{O}-Catalyzed Coupling of Organozinc Iodide Reagents with Bromopyridines: Synthesis of Selectively Protected Pyridine-Containing Azamacrocycles," Journal of Org. Chem. vol. 67, 2002, p. 1407-1410.
International Search Report dated Dec. 22, 2014, issued in PCT/EP2014/074212.
Wünsch, "Catalytic Hydrogenation", Science of Synthesis, 2009, vol. 40, pp. 29-64.
Blaser, "1.2 Heterogeneous Hydrogenation: a Valuable Tool for the Synthetic Chemist", Transition Metals for Organic Synthesis, vol. 2, 2nd Edition 2004 Wiley-VCH: Weinheim.
Fieser and Fieser, Reagents for Organic Synthesis, vol. 1, Wiley: NY, 1974, pp. 723-730.
Tafesh, "A Review of the Selective Catalytic Reduction of Aromatic Nitro Compounds into Aromatic Amines, Isocyanates, Carbamates, and Ureas Using CO" Chem. Rev. 1996, vol. 96, pp. 2035-2052.
Freifedler Practical Catalytic Hydrogenation Techniques and Applications Wiley: New York, 1971, 1-83, pp. 238-260.
Augustine, "Heterogeneous Catalysis for the Synthetic Chemist", Dekker, New York, 1995, pp. 218-219.
Koel, "Promoters and Poisons", Handbook of Heterogeneous Catalysis Published Online: Mar. 15, 2008, pp. 1593-1594.
Horner, "Versuche zum Vorgang der Wasserstoffübertragung, VI, Strukturelle Abhangigkeit Der Giftwirkung Organischer Substanzen Auf Raney-Nickel Als Hydrierungskatalysator", Justus Liebigs Annalen der Chemie, 1962, vol. 660, pp. 1-23.

*Primary Examiner* — David K O'Dell
(74) *Attorney, Agent, or Firm* — McBee Moore Woodward & Vanik IP, LLC

(57) ABSTRACT

The present invention relates to a novel catalytic hydrogenation of substituted 2-methyl cyanopyridyl derivatives, in particular 3-chloro-5-(trifluoromethyl)pyridin-2-yl]acetonitrile [=Py-CN] to substituted 2-ethylaminopyridine derivatives, in particular 2-[3-chloro-5-(trifluoromethyl)pyridin-2-yl]ethanamine [=Py-ethanamine] or salts thereof in the presence of metal catalysts, in particular palladium catalysts.

20 Claims, No Drawings

CATALYTIC HYDROGENATION OF NITRILES

CROSS-REFERENCE TO RELATED APPLICATIONS

This application is a divisional application of U.S. patent application Ser. No. 15/033,987, filed 3 May 2016, which is a 371 National Stage entry of PCT/EP2014/074212, filed 11 Nov. 2014, which claims priority to EP 13193164.4, filed 15 Nov. 2013. The disclosures of the priority applications are incorporated in their entirety herein by reference.

BACKGROUND

Field of the Invention

The present invention relates to a novel catalytic hydrogenation of substituted 2-methyl cyanopyridyl derivatives, wherein the substitution is present on the pyridine ring, in particular 3-chloro-5-(trifluoromethyl)pyridin-2-yl]acetonitrile [=Py-CN] to the corresponding substituted 2-ethylaminopyridine derivatives, in particular 2-[3-chloro-5-(trifluoromethyl)pyridin-2-yl]ethanamine [=Py-ethanamine] or salts thereof in the presence of metal catalysts such as in particular palladium catalysts.

Description of Related Art

Substituted 2-methyl cyanopyridyl derivatives, wherein the substitution is present on the pyridine ring, such as in particular 3-chloro-5-(trifluoromethyl)pyridin-2-yl]acetonitrile are important intermediates for the preparation of Fluopyram (N-[2-[3-chloro-5-(trifluoromethyl)-2-pyridinyl]ethyl]-2-(trifluoromethyl)benzamide), a commercially available fungicide, according to formula (Ia) shown below

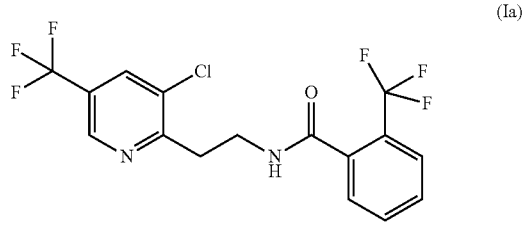 [SMILES: O=C(NCCc1ncc(C(F)(F)F)cc1Cl)c1ccccc1C(F)(F)F]

(Ia)

The production of Fluopyram is disclosed in WO-A 2004/16088.

In general the catalytic hydrogenation of nitriles is well known in the literature and can be carried out with different catalysts under either acidic or basic condition (Nishimura in "Handbook of Heterogeneous Catalytic Hydrogenation for Organic Synthesis", pp. 254-285, John Wiley and Sons, New York, 2001). It is also known that the catalytic hydrogenation of nitriles to the desired primary amines is usually accompanied by the formation of significant amounts of secondary and tertiary amines which contaminate the desired primary amine and makes the isolation very complicated, costly and inefficient and thus not suitable for being used on an industrial scale.

The catalytic hydrogenation of a substituted 2-methyl cyanopyridyl derivative to a substituted 2-ethylaminopyridine derivative according to formula (III) or its corresponding ammonium salt under hydrogen pressure in the presence of a metal catalyst in a protic solvent is described in WO 2004/016088 and EP-A 1674455. WO-A 2004/016088 and EP-A 1 674 455 disclose concretely the catalytic reduction of [3-chloro-5-(trifluoromethyl)pyridin-2-yl]acetonitrile [Py-CN] into [3-chloro-5-(trifluoromethyl)pyridin-2-yl] ethanamine [Py-ethanamine] in the presence of a palladium catalyst on charcoal in a protic solvent being acetic acid. The method described in WO-A 2004/016088 and EP-A 1 674 455 has the drawback in that the yield of the hydrogenation reaction of [Py-CN] followed by hydrolysis of the N-acetyl intermediate to [Py-ethanamine] is low. Another difficulty with this process is the potential for catalyst deactivation by the large amount of side products formed which could amount up to 60% of the end product. Side products include but are not limited to dechlorinated compounds, in particular of 2-[5-(trifluoromethyl)pyridin-2-yl]ethanamine. The low selectivity to the desired product and the formation of different side products makes the economic isolation of the compound according to formula (III) not acceptable at an industrial scale.

It is known in the prior art to improve the hydrogenation of nitriles to the corresponding amines in the presence of an acylating agent. For example, EP-A 1 674 455 discloses a two step synthesis of substituted 2-ethylaminopyridine derivatives comprising the catalytic reduction of reaction of a 2-methylcyanopyridine derivative in the presence of an acylating agent and of a catalyst, in a solvent, under a hydrogen pressure to provide the respective 2-ethylaminopyridyl derivative.

The catalytic hydrogenation step is performed in the presence of an excess of four equivalents of acetanhydride ($Ac_2O$). After hydrolysis of the intermediate the desired product was formed with significant amounts of side product. In addition, this method does not disclose any workup procedure nor recycling process of the expensive palladium catalyst. In addition, the reaction mixture contains large amounts of hydrochloric acid and is therefore highly corrosive. The solvent methanol reacts with the hydrochloric acid forming the gas chloromethane which is toxic and needs to be separated. Consequently the process described is disadvantageous from the economic, environmental and safety standpoint.

WO 2004/041210 relates to compounds, which are useful in the treatment of bacterial infections. Therein, the preparation of a substituted pyridinyl carbamate is mentioned, comprising the step of reacting a substituted pyridinyl acetonitrile compound to the corresponding substituted pyridinyl amine compound in THF under addition of $BH_3.THF$ and HCl, followed by NaOH addition and extraction with EtOAc. However, therein no presence of a metal catalyst, particularly no palladium catalyst, is mentioned.

WO 2008/125839 relates to specific pyrimidine compounds and the pharmaceutical use thereof. Therein, the preparation of 2-(6-methyl-pyridin-2-yl) ethanamine from the corresponding pyridine-2-yl acetonitrile in THF under addition of borane dimethyl sulfide complex in THF and subsequent addition of HCL is mentioned. However, therein no presence of a metal catalyst, particularly no palladium catalyst, is mentioned.

WO 2011/047156 relates to small molecule heterocyclic inhibitors of sepiapterin reductase and the medical use thereof. Therein, the reaction of a chlorine substituted pyridinyl acetonitrile compound to the corresponding chlorine substituted pyridinyl ethanamine compound in THF under addition of $BH_3.DMS$. However, therein neither acid addition nor the presence of a metal catalyst, particularly no palladium catalyst, is mentioned.

Skerlj et al. (Journal of Organic Chemistry, Vol. 67, No. 4, 2002, pages 1407-1410) relates to the synthesis of azamacrocyles, wherein the ring nitrogens are regioselectively functionalized. Therein, an organozinc palladium catalysed coupling with a functionalized bromopyridine is carried out. However, therein only a borane reduction followed by a so-called Nehishi coupling but no catalytic hydrogenation is carried out. In any case, the borane reduction reaction as described therein is not suitable in large scale production as it makes use and leads to undesired reaction products and is expensive.

None of the described prior art processes is suitable for a large scale production. In contrast, the new process of the present invention, as described in detail hereinafter, provides an economic process with significantly reduced formation of unwanted toxic side-products, particularly with reduced formation of unwanted dehalogenated side-products, and remarkably increased yield of the desired reaction products.

The chemoselective catalytic hydrogenation of nitriles according to formula (II) as disclosed below wherein at least one of the X substituents is halogen is in general problematic. Such compounds are easily dehalogenated during the catalytic hydrogenation thus forming undesired dehalogenated side-products.

A respective 2-methyl cyanopyridyl derivative according to formula (II), wherein at least one X substituent is halogen, preferably chlorine, can be defined by the following formula (II') below. Upon dehalogenation during the catalytic hydrogenation process, the corresponding dehalogenated compounds of formula (II''), as defined below, can be formed.

(III) from substituted 2-methyl cyanopyridyl derivatives of the formula (II), as defined below.

The object was achieved according to the present invention by a process (A) for preparing substituted 2-ethylaminopyridine derivatives of the formula (III) and corresponding salts thereof,

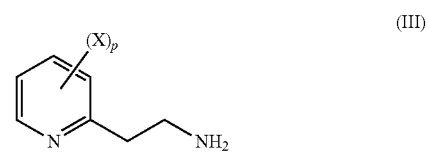

(III)

wherein p is an integer equal to 1, 2, 3 or 4;
each substituent X is chosen, independently of the others, as being halogen, $C_1$-$C_4$ alkyl or $C_1$-$C_4$ haloalkyl;
characterized in that
in step (A1) a substituted 2-methyl cyanopyridyl derivative according to formula (II)

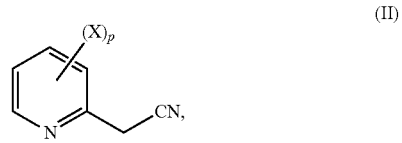

(II)

| Halogen substituted compound (preferably chlorine substituted compound) | corresponding dehalogenated compound (preferably dechlorinated compound) |
|---|---|
| 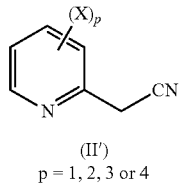 (II') p = 1, 2, 3 or 4 | 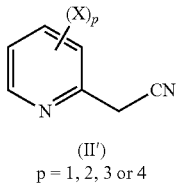 (II') p = 1, 2, 3 or 4 |
| each substituent X is chosen, independently of the others, as being hydrogen, halogen, $C_1$-$C_4$ alkyl or $C_1$-$C_4$ haloalkyl with the proviso that at least one substituent X is halogen, preferably chlorine | each substituent X is chosen, independently of the others, as being hydrogen, halogen, $C_1$-$C_4$ alkyl or $C_1$-$C_4$ haloalkyl with the proviso that the at least one halogen substituent, preferably chlorine substituent, of the corresponding compound (II') is replaced by hydrogen |

The tendency of a halogen-containing compound to dehalogenate during catalytic hydrogenation is higher for bromine- than for chlorine-containing compounds and higher for two- or more fold substituted compounds than for onefold substituted compounds. (cf. Nishimura in "Handbook of Heterogeneous Catalytic Hydrogenation for Organic Synthesis", pp. 623-637, John Wiley and Sons, New York, 2001). A large number of methods with different additives have been developed to reduce the hydrodehalogenation of aromatic compounds. Most of these additives have drawbacks such as low chemoselectivity, undesired side products, costs and toxicity.

SUMMARY

It is therefore an object of the present invention to provide a novel, safer, more economically and environmentally viable process suitable for industrial scale for preparing substituted 2-ethylaminopyridine derivatives of the formula wherein p is an integer equal to 1, 2, 3 or 4;
each substituent X is chosen, independently of the others, as being halogen, $C_1$-$C_4$ alkyl or $C_1$-$C_4$ haloalkyl;
is hydrogenated in the presence of a metal catalyst, a catalyst modifier, and an acid.

DETAILED DESCRIPTION OF A PREFERRED EMBODIMENT

Process (A) may comprise an additional step (A2) after step (A1),
wherein the solvent of the reaction solution comprising the 2-ethylaminopyridine derivative according to formula (III) is removed;
Process (A) may comprise an additional step (A3) after steps (A1) and (A2),
wherein a base is added to the remaining residue of step (A2);

Process (A) may comprise an additional step (A4) after steps (A1), (A2), and (A3),
wherein the organic phase (non-water soluble) is separated from the water phase;
Process (A) may comprise an additional step (A5) after steps (A1), (A2), (A3), and (A4),
wherein the precipitated product according to formula (III) is isolated from the reaction suspension comprising the 2-ethylaminopyridine derivative according formula (III);
Process (A) may comprise an additional step (A6) after steps (A1), (A2), (A3), (A4) and (A5),
wherein the isolated product according to formula (III) is reacted with a benzoyl halide according to formula (IV)

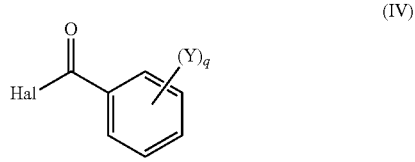

wherein
Hal is fluorine, chlorine or bromine;
q is an integer equal to 1, 2, 3 or 4;
each substituent Y is chosen, independently of the others, as being halogen, $C_1$-$C_4$ alkyl or $C_1$-$C_4$ haloalkyl;
to the compound according to formula (I)

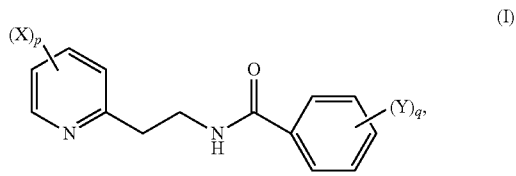

wherein p and X are defined as above;
q is an integer equal to 1, 2, 3 or 4;
each substituent Y is chosen, independently of the others, as being halogen, $C_1$-$C_4$ alkyl or $C_1$-$C_4$ haloalkyl.
Optionally in step (A1) and (A3) a solvent can be added.
Optionally in step (A4) acid can be added to the organic phase.
Optionally in step (A4) remaining water can be removed.
Optionally in step (A5) the reaction suspension is taken up with a further amount of solvent.
p is preferably 1 or 2.
p is very preferably 2.
In each case, X is preferably independently of the others, as being fluorine, chlorine, bromine, $C_1$-$C_2$ alkyl or $C_1$-$C_2$ haloalkyl having 1 to 5 halogen atoms selected independently from each other from fluorine, chlorine;
In each case, X is more preferably independently of the others, as being fluorine, chlorine, methyl, ethyl or $C_1$-$C_2$ haloalkyl having 1 to 5 halogen atoms selected independently from each other from fluorine, chlorine;
In each case, X is particular preferably independently of the others, as being fluorine, chlorine, or difluoromethyl, trifluoromethyl, dichloromethyl, trichloromethyl;
In each case, X is very particular preferably independently of the others, as being chlorine, or trifluoromethyl.
As regards the positions in which the 2-pyridyl moiety is substituted by X, the 2-pyridyl moiety is preferably substituted by X in 3- and/or in 5-position. Preferably, the 2-pyridyl moiety is substituted by X in 3- and 5-position.
q is preferably 1 or 2.
q is very preferably 1.
Y is preferably independently of the others, as being fluorine, chlorine, bromine, $C_1$-$C_2$ alkyl or $C_1$-$C_2$ haloalkyl having 1 to 5 halogen atoms selected independently from each other from fluorine, chlorine;
Y is more preferably independently of the others, as being fluorine, chlorine, methyl, ethyl or $C_1$-$C_2$ haloalkyl having 1 to 5 halogen atoms selected independently from each other from fluorine, chlorine;
Y is particular preferably independently of the others, as being fluorine, chlorine, or difluoromethyl, trifluoromethyl, dichloromethyl, trichloromethyl;
Y is very particular preferably trifluoromethyl.
Y is very particular preferably chlorine.
As regards the positions in which the phenyl moiety is substituted by Y, the phenyl moiety is preferably substituted by Y in 2- and/or in 6-position. Preferably, the phenyl moiety is substituted by Y in 2-position.
Very particular preferably the compound according to formula (II) is 3-chloro-5-(trifluoromethyl)pyridin-2-yl]acetonitrile and the compound according to formula (III) is 2-[3-chloro-5-(trifluoromethyl)pyridin-2-yl]ethanamine.
Very preferably the compound according to formula (IV) is 2-trifluoromethyl-benzoyl chloride.
Very preferably the compound according to formula (I) is fluopyram as defined in formula (Ia).
The corresponding salts of the compounds according to formula (I) are preferably hydrogensulfates, sulfates, hydrochlorides, phosphates, formates, or acetates.
Preferably step (A6) is performed in the presence of a base.
Useful bases which may be used in the process according to the present invention, such as in particular in step (A3) and/or (A6) are inorganic or organic bases such as $Na_2CO_3$, $NaHCO_3$, $K_2CO_3$, $KHCO_3$, NaOH, KOH, $Ca(OH)_2$, $Mg(OH)_2$, triethyl amine, N,N-diisopropylethylamine.
The following bases are particularly preferred for step (A3): $Na_2CO_3$, $NaHCO_3$, $K_2CO_3$, $KHCO_3$, NaOH, KOH, $Ca(OH)_2$. More preferred are NaOH, KOH, $Ca(OH)_2$. Mostly preferred are NaOH, KOH. Preferably, in step (A3) a base as defined herein is added until adjustment of the pH value of the reaction solution to pH 4 to 14, preferably pH 6 to 13 is achieved.
The following bases are particularly preferred for step (A6): $Na_2CO_3$, $NaHCO_3$, $K_2CO_3$, $KHCO_3$, NaOH, KOH, $Ca(OH)_2$. More preferred are NaOH, KOH, $Ca(OH)_2$. Mostly preferred are NaOH, KOH. Preferably, in step (A6) a base as defined herein is added until adjustment of the pH value of the reaction solution to pH 4 to 14, preferably pH 6 to 13 is achieved.
The corresponding salts of the compounds according to formula (III) are preferably hydrogen sulfates, sulfates, hydrochlorides, dihydrogen phosphates, hydrogen phosphates, phosphates, mesylates, citrates, formates, or acetates.
The metal catalyst is any hydrogenation catalyst selected from the group of palladium, platinum, ruthenium, and rhodium catalysts. In one embodiment the metal catalyst is any hydrogenation catalyst selected from the group of palladium, platinum, and ruthenium catalysts.
In one embodiment the metal catalyst is any hydrogenation catalyst selected from the group of palladium, platinum, and rhodium catalysts. Palladium (Pd), platinum (Pt) or a combination thereof as catalysts are preferred catalytically active metal catalysts. Palladium (Pd), platinum (Pt) or a combination thereof or Rhodium catalysts are preferred catalytically active metal catalysts. Particularly preferred are palladium catalysts. Even more preferred are palladium catalysts from the group consisting of elemental palladium and palladium compounds which are reducible by hydrogen or any other reducing agents (e.g. sodium formate, hydrazine) to elemental palladium at the hydrogenation conditions as applied in the process of the present invention, and mixtures thereof.

The metal catalysts may be present in any chemical form, for example in elemental, colloidal, salt or hydroxide, oxide form, together with complexing agents as chelates. The metal catalysts may be present in supported form, i.e. applied to any support, preferably an organic or inorganic support. Examples of suitable supports are carbon (charcoal or activated carbon), aluminium oxide, silicon dioxide, zirconium dioxide, titanium dioxide, calcium carbonate, barium sulphate and zeolite. Preferred supports are carbon such as charcoal and activated carbon.

The metal loading on such a support is between 0.01% and 100%, more preferably in the range of 0.5% to 50% and even more preferably in the range of 0.5% to 25%, and most preferably in the range of 1% to 20% and between 5% and 20%. Further preferred ranges further include a metal loading on such support between 0.5% and 10%, between 0.5% and 20%, between 1% and 10%, between 1% and 5%, between 1% and 3%, between 3% and 10%, between 3% and 20%, and between 5% and 10%.

Preferred catalysts in supported form are selected from palladium and platinum catalysts, with palladium catalysts in supported form being particularly preferred.

Therefrom, preferred catalysts, which are present in supported form, are Pd/C, Pd(OH)$_2$/C, Palladium oxide/C, mixed Palladium oxide-hydroxide/C, Palladium oxide/Al$_2$O$_3$, mixed Palladium oxide-hydroxide/Al$_2$O$_3$, Palladium oxide/SiO$_2$, mixed Palladium oxide-hydroxide/SiO$_2$, Pd/CaCO$_3$, Pd/C-diphenylsulfide, Pd/Al$_2$O$_3$, Pd/SiO$_2$, Pd/BaSO$_4$, Pd(II)acetate-Polymethylhydrosiloxane, Pd(Fe)/C, Pd/C 5% sulfur, Pt/C, Pt/C-5% sulfur, Pt/Al$_2$O$_3$.

Further suitable catalysts are Pd/V catalysts such as 5% Pd/0.5% V, Pd/Pt catalysts such as 4% Pd/1% Pt.

Particularly preferred catalysts, which are present in supported form, are Pd/C, Pd/Al$_2$O$_3$, Pd(OH)$_2$/C, Palladium oxide/C, mixed Palladium oxide-hydroxide/C, Palladium oxide/Al$_2$O$_3$, mixed Palladium oxide-hydroxide/Al$_2$O$_3$, Palladium oxide/SiO$_2$, mixed Palladium oxide-hydroxide/SiO$_2$, Pd/SiO$_2$.

Very particularly preferred catalysts are Pd/C, Pd/Al$_2$O$_3$, Pd(OH)$_2$/C, Palladium oxide/C, mixed Palladium oxide-hydroxide/C, Palladium oxide/Al$_2$O$_3$, mixed Palladium oxide-hydroxide/Al$_2$O$_3$, Palladium oxide/SiO$_2$, mixed Palladium oxide-hydroxide/SiO$_2$, Pd/SiO$_2$ having a metal loading in the range of 0.5% to 25%, preferably in the range of 0.5% to 25%, more preferably in the range of 1% to 20%, even more preferably in the range of 3 to 20%, most preferably in the range of 5 to 20%.

Very particularly preferred catalysts are

1% to 25%, preferably 2% to 20%, preferably 3% to 20%, preferably 5% to 20% Pd/C, 1% to 25%, preferably 2% to 20%, preferably 3% to 20%, preferably 5% to 20% Pd/Al$_2$O$_3$, 1% to 25%, preferably 2% to 20%, preferably 3% to 20%, preferably 5% to 20% Pd(OH)$_2$/C, 1% to 25%, preferably 2% to 20%, preferably 3% to 20%, preferably 5% to 20% Palladium oxide/C, 1% to 25%, preferably 2% to 20%, preferably 3% to 20%, preferably 5% to 20% mixed Palladium oxide-hydroxide/C, 1% to 25%, preferably 2% to 20%, preferably 3% to 20%, preferably 5% to 20% Palladium oxide/Al$_2$O$_3$, 1% to 25%, preferably 2% to 20%, preferably 3% to 20%, preferably 5% to 20% mixed Palladium oxide-hydroxide/Al$_2$O$_3$, 1% to 25%, preferably 2% to 20%, preferably 3% to 20%, preferably 5% to 20% Palladium oxide/SiO$_2$, 1% to 25%, preferably 2% to 20%, preferably 3% to 20%, preferably 5% to 20% mixed Palladium oxide-hydroxide/SiO$_2$, 1% to 25%, preferably 2% to 20%, preferably 3% to 20%, preferably 5% to 20% Pd/SiO$_2$.

Very particularly preferred catalysts are 1% Pd/C, 1% Pd/Al$_2$O$_3$, 1% Pd(OH)$_2$/C, 1% Palladium oxide/C, 1% mixed Palladium oxide-hydroxide/C, 1% Palladium oxide/Al$_2$O$_3$, 1% mixed Palladium oxide-hydroxide/Al$_2$O$_3$, 1% Palladium oxide/SiO$_2$, 1% mixed Palladium oxide-hydroxide/SiO$_2$, 1% Pd/SiO$_2$.

Very particularly preferred catalysts are 2% Pd/C, 2% Pd/Al$_2$O$_3$, 2% Pd(OH)$_2$/C, 2% Palladium oxide/C, 2% mixed Palladium oxide-hydroxide/C, 2% Palladium oxide/Al$_2$O$_3$, 2% mixed Palladium oxide-hydroxide/Al$_2$O$_3$, 2% Palladium oxide/SiO$_2$, 2% mixed Palladium oxide-hydroxide/SiO$_2$, 2% Pd/SiO$_2$.

Very particularly preferred catalysts are 3% Pd/C, 3% Pd/Al$_2$O$_3$, 3% Pd(OH)$_2$/C, 3% Palladium oxide/C, 3% mixed Palladium oxide-hydroxide/C, 3% Palladium oxide/Al$_2$O$_3$, 3% mixed Palladium oxide-hydroxide/Al$_2$O$_3$, 3% Palladium oxide/SiO$_2$, 3% mixed Palladium oxide-hydroxide/SiO$_2$, 3% Pd/SiO$_2$.

Very particularly preferred catalysts are 4% Pd/C, 4% Pd/Al$_2$O$_3$, 4% Pd(OH)$_2$/C, 4% Palladium oxide/C, 4% mixed Palladium oxide-hydroxide/C, 4% Palladium oxide/Al$_2$O$_3$, 4% mixed Palladium oxide-hydroxide/Al$_2$O$_3$, 4% Palladium oxide/SiO$_2$, 4% mixed Palladium oxide-hydroxide/SiO$_2$, 4% Pd/SiO$_2$.

Very particularly preferred catalysts are 5% Pd/C, 5% Pd/Al$_2$O$_3$, 5% Pd(OH)$_2$/C, 5% Palladium oxide/C, 5% mixed Palladium oxide-hydroxide/C, 5% Palladium oxide/Al$_2$O$_3$, 5% mixed Palladium oxide-hydroxide/Al$_2$O$_3$, 5% Palladium oxide/SiO$_2$, 5% mixed Palladium oxide-hydroxide/SiO$_2$, 5% Pd/SiO$_2$.

Very particularly preferred catalysts are 7% Pd/C, 7% Pd/Al$_2$O$_3$, 7% Pd(OH)$_2$/C, 7% Palladium oxide/C, 7% mixed Palladium oxide-hydroxide/C, 7% Palladium oxide/Al$_2$O$_3$, 7% mixed Palladium oxide-hydroxide/Al$_2$O$_3$, 7% Palladium oxide/SiO$_2$, 7% mixed Palladium oxide-hydroxide/SiO$_2$, 7% Pd/SiO$_2$.

Very particularly preferred catalysts are 10% Pd/C, 10% Pd/Al$_2$O$_3$, 10% Pd(OH)$_2$/C, 10% Palladium oxide/C, 10% mixed Palladium oxide-hydroxide/C, 10% Palladium oxide/Al$_2$O$_3$, 10% mixed Palladium oxide-hydroxide/Al$_2$O$_3$, 10% Palladium oxide/SiO$_2$, 10% mixed Palladium oxide-hydroxide/SiO$_2$, 10% Pd/SiO$_2$.

Very particularly preferred catalysts are 15% Pd/C, 15% Pd/Al$_2$O$_3$, 15% Pd(OH)$_2$/C, 15% Palladium oxide/C, 15% mixed Palladium oxide-hydroxide/C, 15% Palladium oxide/Al$_2$O$_3$, 15% mixed Palladium oxide-hydroxide/Al$_2$O$_3$, 15% Palladium oxide/SiO$_2$, 15% mixed Palladium oxide-hydroxide/SiO$_2$, 15% Pd/SiO$_2$.

Very particularly preferred catalysts are 20% Pd/C, 20% Pd/Al$_2$O$_3$, 20% Pd(OH)$_2$/C, 20% Palladium oxide/C, 20% mixed Palladium oxide-hydroxide/C, 20% Palladium oxide/

Al$_2$O$_3$, 20% mixed Palladium oxide-hydroxide/Al$_2$O$_3$, 20% Palladium oxide/SiO$_2$, 20% mixed Palladium oxide-hydroxide/SiO$_2$, 20% Pd/SiO$_2$.

Very particularly preferred catalysts are 25% Pd/C, 25% Pd/Al$_2$O$_3$, 25% Pd(OH)$_2$/C, 25% Palladium oxide/C, 25% mixed Palladium oxide-hydroxide/C, 25% Palladium oxide/Al$_2$O$_3$, 25% mixed Palladium oxide-hydroxide/Al$_2$O$_3$, 25% Palladium oxide/SiO$_2$, 25% mixed Palladium oxide-hydroxide/SiO$_2$, 25% Pd/SiO$_2$.

The catalysts are available from commercial sources like the companies BASF, Acros, Evonik.

The catalysts can be used in any form, for example dry, or wet (water-wet). Preferably, the catalysts are used several times. More preferably, the catalysts are used more than two times. Most preferably, the catalysts are used between two times and 10 times. The catalysts can be used in a batch, semibatch or fixed bed hydrogenation reaction as well as in a continuous hydrogenation reaction process. More preferably the catalysts can be used in a batch or fixed bed hydrogenation reaction.

In the process according to the invention, the catalyst is used in a concentration of about 0.01 mol % to about 50 mol % catalyst with respect to the amount of cyanopyridyl derivative according to formula (II). The catalyst is preferably used in a concentration of about 0.1 to about 50 mol %, more preferably the catalyst is used in a concentration of about 0.5 mol % to about 3 mol %.

Catalyst modifiers are such compounds which are capable of modifying the activity of the catalyst in such a way that the dehalogenation, in particular the dechlorination, of a halogen substituted, particularly chlorine substituted, 2-methyl cyanopyridyl derivative according to formula (II) and (II'), as defined above, by forming the dehalogenated, particularly dechlorinated, corresponding compound of formula (II"), as defined above, is reduced compared to the reaction without the catalyst modifier. Whilst not being bound by theory, in the process of the present invention the modifier influences, in particular attenuates the activity of the metal catalyst, in particular of the palladium catalysts and thus reduces the formation of the unwanted dehalogenated, particularly the dechlorinated, side-products. One the one hand, this reduces the toxicity and on the other hand enhances the yield of the desired reaction products.

By using the catalyst modifier in the process of the present invention a reduction of the dehalogenated, particularly dechlorinated, side-products is achieved, preferably to equal or less than 25%, more preferably equal or less than 20%, even more preferably equal or less than 15%, particular more preferably equal or less than 10%, even particular more preferably equal or less than 5%, most preferably equal or less than 3%, most particular preferably equal or less than 1%, can be achieved. It is in particular possible to reduce the amount of dehalogenated, particularly dechlorinated, side-products by a factor of at least 6, preferably of at least 10, more preferably of at least 30 compared to the respective reaction without using the modifier.

Suitable catalyst modifiers are organic or inorganic sulfur-containing compounds such as thiophene, tetrahydrothiophene, 2-mercaptophenol, cysteine, 3,6-dithia 1,8 octadiol, 2,2'-thiobisethanol, diphenyl sulfide, thiophenol, thioanisole, sulfolane, thiourea, Na$_2$S$_2$O$_3$-xH$_2$O, Na$_2$S, amines such as alkylamines, benzylamines, pyridines, morpholines, polyamines, amidines (e.g. chinoline); a inorganic or organic compounds comprising phosphor e.g. PPh$_3$; molybdenum containing compounds e.g. Mo(CO)$_6$ Vanadium oxides or sulfides e.g. V(V) oxide, V(IV) oxide, V(III) sulfide, NH$_4$VO$_3$; Lewis acids (e.g. ZnBr$_2$, ZnCl$_2$, MgBr$_2$, MgO, salts comprising Fe e.g. FeCl$_2$, FeCl$_3$, Fe(OAc)$_2$); tetraalkylammonium salts (e.g. iodides, bromides and chlorides) such as n-tetramethylammonium iodide, n-tetraethylammonium iodide, n-tetrabutylammonium iodide, n-tetramethylammonium bromide (TMAB), n-tetraethylammonium bromide, n-tetrabutylammoniumbromide (TBAB), n-tetramethylammonium chloride, n-tetraethylammonium chloride, n-tetrabutylammoniumchloride; inorganic salts such as halides (e.g. NaCl, NaBr, NaI, KCl, KBr, KI, LiBr) or MgBr$_2$, AlCl$_3$, CeCl$_3$, CuCl, CuBr, CuI, CuBr$_2$, Suitable catalyst modifiers are organic or inorganic sulfur-containing compounds such as thiophene, tetrahydrothiophene, 2-mercaptophenol, cysteine, 3,6-dithia 1,8 octadiol, 2,2'-thiobisethanol, diphenyl sulfide, thiophenol, thioanisole, sulfolane, thiourea, Na$_2$S$_2$O$_3$-xH$_2$O, Na$_2$S; amines such chinoline, inorganic or organic compound comprising phosphor e.g. PPh$_3$; molybdenum containing compounds e.g. Mo(CO)$_6$, Vanadium oxides or sulfides e.g. V(V) oxide, V(IV) oxide, V(III) sulfide, NH$_4$VO$_3$; Lewis acids (e g ZnBr$_2$, ZnCl$_2$, MgBr$_2$, MgO, salts comprising Fe e. g. FeCl$_2$, FeCl$_3$, Fe(OAc)$_2$); tetraalkylammonium salts (e.g. iodides, bromides and chlorides) such as n-tetramethylammonium iodide, n-tetraethylammonium iodide, n-tetrabutylammonium iodide, n-tetramethylammonium bromide (TMAB), n-tetraethylammonium bromide, n-tetrabutylammoniumbromide (TBAB), n-tetramethylammonium chloride, n-tetraethylammonium chloride, n-tetrabutylammoniumchloride; inorganic salts such as halides (e. g. NaCl, NaBr, NaI, KCl, KBr KI, LiBr,) or MgBr$_2$, AlCl$_3$, CeCl$_3$, CuCl, CuBr, CuI, CuBr$_2$.

Suitable catalyst modifiers being organic sulfur-containing compounds are selected from the group consisting of thiophene, tetrahydrothiophene, 2-mercaptophenol, cysteine, 3,6-dithia 1,8 octadiol, 2,2'-thiobisethanol, diphenyl sulfide, thiophenol, thioanisole, sulfolane, thiourea, Na$_2$S$_2$O$_3$-xH$_2$O, Na$_2$S.

Preferred suitable catalyst modifiers being organic sulfur-containing compounds are selected from the group consisting of, tetrahydrothiophene, 2-mercaptophenol, cysteine, 3,6-dithia 1,8 octadiol, thiourea.

Preferred suitable catalyst modifiers being inorganic or organic compounds comprising phosphor are selected from the group consisting of PPh$_3$.

Preferred suitable catalyst modifiers being molybdenum containing compounds are selected from the group consisting of Mo(CO)$_6$ Preferred suitable catalyst modifiers being Vanadium oxides or sulfides are selected from the group consisting of V(V) oxide, V(IV) oxide, V(III) sulfide, NH$_4$VO$_3$.

Suitable catalyst modifiers being Lewis acids are selected from the group consisting of ZnBr$_2$, ZnCl$_2$, MgBr$_2$, MgO, Fe, FeCl$_2$, FeCl$_3$, Fe(OAc)$_2$.

Preferred suitable catalyst modifiers being Lewis acids are selected from the group consisting of ZnBr$_2$, FeCl$_3$, Fe(OAc)$_2$.

Suitable catalyst modifiers being tetraalkylammonium salts are selected from the group consisting of tetramethylammonium iodide, n-tetraethylammonium iodide, n-tetrabutylammonium iodide, n-tetramethylammonium bromide (TMAB), n-tetraethylammonium bromide, n-tetrabutylammoniumbromide (TBAB), n-tetramethylammonium chloride, n-tetraethylammonium chloride, n-tetrabutylammoniumchloride.

Preferred suitable catalyst modifiers being tetraalkylammonium salts are selected from the group consisting of n-tetramethylammonium bromide (TMAB), n-tetrabutylammoniumbromide (TBAB).

Suitable catalyst modifiers being inorganic salts are selected from the group consisting of NaCl, NaBr, NaI, KCl, KBr, KI, LiBr, MgBr$_2$, AlCl$_3$, CeCl$_3$, CuCl, CuBr, CuI, CuBr$_2$.

Preferred suitable catalyst modifiers being inorganic salts are selected from the group consisting of NaBr, NaI, KBr, KI, CuI.

Suitable catalyst modifies being amines are alkylamines, benzylamines, pyridines, morpholines, polyamines, amidines (e.g. chinoline).

A preferred suitable catalyst modifier being amines is chinoline.

More preferred catalyst modifiers are selected from a) being organic sulfur-containing compounds selected from the group consisting of thiophene, tetrahydrothiophene, 2-mercaptophenol, cysteine, 3,6-dithia 1,8 octadiol, 2,2'-thiobisethanol, diphenyl sulfide, thiophenol, thioanisole, sulfolane, thiourea, Na$_2$S$_2$O$_3$-xH$_2$O, Na$_2$S;

b) being Vanadium oxides or sulfides selected from the group consisting of V(V) oxide, V(IV) oxide, V(III) sulfide, NH$_4$VO$_3$;

c) being inorganic or organic compounds comprising phosphor are selected from the group consisting of PPh$_3$;

d) being Lewis acids selected from the group consisting of ZnBr$_2$, ZnCl$_2$, MgBr$_2$, MgO, FeCl$_2$, FeCl$_3$, Fe(OAc)$_2$.

e) being tetraalkylammonium salts selected from the group consisting of tetramethylammonium iodide, n-tetraethylammonium iodide, n-tetrabutylammonium iodide, n-tetramethylammonium bromide (TMAB), n-tetraethylammonium bromide, n-tetrabutylammoniumbromide (TBAB), n-tetramethylammonium chloride, n-tetraethylammonium chloride, n-tetrabutylammoniumchloride.

f) being inorganic salts selected from the group consisting of NaCl, NaBr, NaI, KCl, KBr, KI, LiBr, MgBr$_2$, AlCl$_3$, CeCl$_3$, CuCl, CuBr, CuI, CuBr$_2$, g) being molybdenum containing compounds selected from the group consisting of Mo(CO)$_6$, h) being amines selected from the group consisting of chinoline.

Even more preferred catalyst modifiers are selected from a) being organic sulfur-containing compounds selected from the group consisting of tetrahydrothiophene, 2-mercaptophenol, cysteine, 3,6-dithia 1,8 octadiol, thiourea, Na$_2$S$_2$O$_3$-xH$_2$O, Na$_2$S;

b) being Vanadium oxides or sulfides selected from the group consisting of V(V) oxide, V(IV) oxide, V(III) sulfide, NH$_4$VO$_3$;

c) being inorganic or organic compound comprising phosphor are selected from the group consisting of PPh$_3$, d) being Lewis acids selected from the group consisting of ZnBr$_2$, MgO, FeCl$_3$, Fe(OAc)$_2$;

e) being tetraalkylammonium salts selected from the group consisting of n-tetramethylammonium bromide (TMAB), n-tetrabutylammoniumbromide (TBAB);

f) being inorganic salts selected from the group consisting of NaBr, NaI, KBr, KI, CuI, g) being molybdenum containing compounds are selected from the group consisting of Mo(CO)$_6$, h) being amines selected from the group consisting of chinoline.

Preferred catalyst modifiers are sulfur-containing compounds, tetraalkylammonium halides, alkali halides and other metal halides. Further preferred catalyst modifiers are halide containing compounds, particularly such as selected from the halide containing catalyst modifier compounds as defined above. It is further preferred that the catalyst modifiers are selected from the group of aprotic compounds, i.e. from the compounds as listed herein, which cannot donate hydrogen.

More preferred catalyst modifiers are 3,6-dithia-1,8-octadiole, CuI, FeBr$_3$, FeCl$_3$, Fe(OAc)$_2$, KI, KBr, MgBr$_2$, MgO, NaBr, NaI, NH$_4$VO$_3$, chinoline, n-tetramethylammonium iodide, n-tetraethylammonium iodide, n-tetrabutylammonium iodide, n-tetramethylammonium bromide (TMAB), n-tetraethylammonium bromide, n-tetrabutylammoniumbromide (TBAB), n-tetramethylammonium chloride, n-tetraethylammonium chloride, n-tetrabutylammoniumchloride, tetrahydrothiophene, thioethanole, thio urea, V(V) oxide, V(IV) oxide, (V(III) sulfide, ZnBr$_2$.

Even preferred catalyst modifiers are 3,6-dithia-1,8-octadiole, CuI, FeBr$_3$, FeCl$_3$, Fe(OAc)$_2$, KI, KBr, MgBr$_2$, MgO, NaBr, NaI, NH$_4$VO$_3$, chinoline, n-tetramethylammonium bromide, n-tetraethylammonium bromide, n-tetrabutylammoniumbromide, tetrahydrothiophene, thioethanole, thio urea, V(V) oxide, V(IV) oxide, (V(III) sulfide, ZnBr$_2$. Even preferred modifiers are 3,6-dithia-1,8-octadiole, FeBr$_3$, FeCl$_3$, Fe(OAc)$_2$, KBr, MgBr$_2$, MgO, NaBr, NH$_4$VO$_3$, chinoline, n-tetramethylammonium bromide, n-tetraethylammonium bromide, n-tetrabutylammoniumbromide, tetrahydrothiophene, thioethanole, V(V) oxide, V(IV) oxide, ZnBr$_2$.

In one embodiment suitable modifiers are organic sulfur-containing compounds (e.g. thiophene, tetrahydrothiophene, 2,2'-thiobisethanol, diphenyl sulfide, thiophenol, thioanisole, sulfolane, thio urea, MgO, amines such as alkylamines, benzylamines, pyridines, morpholines, polyamines, amidines, phosphorous acids and its derivatives, metal ions and salts, or a combination of inorganic/organic phosphorous with a vanadium or molybdenum compound, Vanadium oxides or sulfides, NH$_4$VO$_3$, Lewis acids (e g ZnBr$_2$, ZnCl$_2$, MgBr$_2$, Fe or salts e. g. FeCl$_2$, FeCl$_3$, Fe(OAc)$_2$), tetraalkylammonium salts (e.g. iodides, bromides and chlorides) inorganic salts such as alkali halides (e. g. NaCl, NaBr, NaI, KCl, KBr KI, LiBr,) or MgBr$_2$, AlCl$_3$, CeCl$_3$, CuCl, CuBr, CuI, CuBr$_2$.

In another embodiment modifiers are sulfur-containing compounds, tetraalkylammonium halides, alkali halides and other metal halides In another embodiment modifiers are 3,6-dithia-1,8-octadiole, CuI, FeBr$_3$, FeCl$_3$, Fe(OAc)$_2$, KI, KBr, MgBr$_2$, MgO, NaBr, NaI, NH$_4$VO$_3$, n-tetramethylammonium iodide, n-tetraethylammonium iodide, n-tetrabutylammonium iodide, n-tetramethylammonium bromide, n-tetraethylammonium bromide, n-tetrabutylammoniumbromide, n-tetramethylammonium chloride, n-tetraethylammonium chloride, n-tetrabutylammoniumchloride, tetrahydrothiophene, thioethanole, thio urea, V(V) oxide, V(IV) oxide, (V(III) sulfide, ZnBr$_2$.

In another embodiment modifiers are 3,6-dithia-1,8-octadiole, CuI, FeBr$_3$, FeCl$_3$, Fe(OAc)$_2$, KI, KBr, MgBr$_2$, MgO, NaBr, NaI, NH$_4$VO$_3$, n-tetramethylammonium bromide, n-tetraethylammonium bromide, n-tetrabutylammoniumbromide, tetrahydrothiophene, thioethanole, thio urea, V(V) oxide, V(IV) oxide, (V(III) sulfide, ZnBr$_2$. Even preferred modifiers are 3,6-dithia-1,8-octadiole, FeBr$_3$, FeCl$_3$, Fe(OAc)$_2$, KBr, MgBr$_2$, MgO, NaBr, NH$_4$VO$_3$, n-tetramethylammonium bromide, n-tetraethylammonium bromide, n-tetrabutylammoniumbromide, tetrahydrothiophene, thioethanole, V(V) oxide, V(IV) oxide, ZnBr$_2$.

In one embodiment the preferred concentrations of the modifiers are in the range from about 0.0000001 equivalents to about 10 equivalents with respect to the amount of cyanopyridyl derivative according to formula (II) used in the reaction, more preferably in the range of 0.001 equivalents to 2 equivalents and most preferably in the range of 0.01 equivalents to 0.1 equivalents.

In a further preferred embodiment of the invention from the definition of the catalyst modifier organic and inorganic acids are excluded. Therein, in particular, organic acids are excluded, more particularly acetic acid and sulfuric acid as well as sulfurous acid are excluded. It is even more preferred, that acetic acid is excluded from the definition of catalyst modifiers according to the present invention.

Further it is preferred that from the aforesaid preferred group of catalyst modifiers comprising sulfur-containing compounds, tetraalkylammonium halides, alkali halides and other metal halides organic and inorganic acids, particularly sulfur-containing acids are excluded.

In a further preferred embodiment of the present invention, a catalyst modifier is used, with organic and/or inorganic acids and/or one or more of the compounds of the group consisting of CuI, NaI, KI, thio urea and V(III) sulphide being excluded.

The preferred concentrations of the catalyst modifiers are in the range from about 0.0000001 equivalents to about 10 equivalents with respect to the amount of cyanopyridyl derivative according to formula (II) used in the reaction, more preferably in the range of 0.0001 equivalents to 2 equivalents and most preferably in the range of 0.0001 equivalents to 0.1 equivalents.

Whilst not being bound by theory, in the process of the present invention the acid is used to mask and thus protect the catalyst, in particular the palladium catalysts. During the hydrogenation reaction free amine compounds are formed which act as a catalyst poison and nearly immediately disable and inactivate the catalyst, thus significantly reducing the yield of the desired reaction products. By using an acid in the hydrogenation process of the present invention, higher recycling rates of the catalysts are possible, which further enhances the yield and an economic process management.

Suitable acids to be used in the hydrogenation reaction according to the invention are proton donating compounds. Preferred are organic acids such as acetic acid ($CH_3CO_2H$), trifluoro acetic acid ($CF_3CO_2H$), citric acid, p-toluenesulfonic acid, methanesulfonic acid, trifluoromethanesulfonic acid, formic acid or inorganic acids such as sulfuric acid ($H_2SO_4$), phosphoric acid ($H_3PO_4$) and hydrochloric acid (HCl). Hydrochloric acid may be used in the form of aqueous and/or gaseous hydrochloric acid.

Preferred acids for the hydrogenation reaction of step (A1) are selected from group consisting of acetic acid ($CH_3CO_2H$), methanesulfonic acid, (aqueous and/or gaseous) HCl and $H_2SO_4$.

More preferred acids for the hydrogenation reaction of step (A1) are selected from group consisting of acetic acid ($CH_3CO_2H$), (aqueous and/or gaseous) HCl and $H_2SO_4$.

More preferred acids for the hydrogenation reaction are selected from group consisting of methanesulfonic acid, (aqueous and/or gaseous) HCl and $H_2SO_4$.

More preferred acids for the hydrogenation reaction are selected from group consisting of acetic acid ($CH_3CO_2H$), (aqueous and/or gaseous) HCl and $H_2SO_4$.

Mostly preferred acids for the hydrogenation reaction are selected from group consisting of (aqueous and/or gaseous) HCl and $H_2SO_4$.

It is preferred to use the organic or inorganic acids as an additive in the hydrogenation reaction according to the invention in concentrations of the acids in the range from about 0.1 equivalents to about 100 equivalents with respect to the amount of cyanopyridyl derivative according to formula (II) used in the reaction, more preferably in the range of 2 equivalents to about 10 equivalents and most preferably in the range of 0.5 equivalents to 2 equivalents.

In the additional steps following the hydrogenation reaction of step (A1) acids can be added, too. In particular, in step (A4) optionally an acid can be added to the organic phase. Therein, the acids as defined above can be used, either alone or in mixtures thereof. Preferably, in step (A4) HCl or $H_2SO_4$ is used, either in aqueous and/or gaseous form. Therein, it is preferred to add the acid in concentrations in the range of 0.1 equivalents to about 100 equivalents, more preferably in the range of 0.2 equivalents to about 10 equivalents, most preferably in the range of 0.5 equivalents to about 5 equivalents.

The hydrogenation reaction can be conducted at any suitable reaction conditions. In general the hydrogenation reaction will be conducted under batch, semi/batch or fixed bed conditions as well as in a continuous hydrogenation reaction process.

In one embodiment the hydrogenation reaction will be conducted under batch or fixed bed conditions.

Therein, the hydrogenation reaction is performed in either batch, semi-batch or continuous slurry reactors. Semi-batch hydrogenation involves the feeding of the nitrile (with or without acid and with or without modifier) to a slurry of catalyst in a solvent (or without). In this mode the ratio of nitrile to the catalyst is lower compared to batch process. In contrast to the batch or semi-batch process in the continuous mode the product is removed at the same rate as nitrile as is added.

According to the present invention the following combinations of catalyst, modifier and acid may be used:

TABLE 1

| Ref. | Catalyst | Ref. | Modifier | Ref. | Acid |
| --- | --- | --- | --- | --- | --- |
| c1 | Pd | m1 | Thiophene | a1 | Sulfuric acid |
| c2 | Pd/C | m2 | Tetrahydrothiophene | a2 | HCl |
| c3 | Pd(OH)$_2$/C | m3 | 2-Mercaptophenol | a3 | Phosphoric acid |
| c4 | Pd/Al$_2$O$_3$ | m4 | Cysteine | a4 | Methanesulfonic acid |
| c5 | Palladium oxide/C | m5 | 3,6-Dithia 1,8 octadiol | | |
| c6 | mixed Palladium oxide-hydroxide/C | m6 | 2,2'-Thiobisethanol | | |
| c7 | Palladium oxide/Al$_2$O$_3$ | m7 | Diphenyl sulfide | | |
| c8 | mixed Palladium oxide-hydroxide/Al$_2$O$_3$ | m8 | Thiophenol | | |
| c9 | Palladium/SiO$_2$ | m9 | Thioanisole | | |
| c10 | Palladium oxide/SiO$_2$ | m10 | Sulfolane | | |
| c11 | mixed Palladium oxide-hydroxide/SiO$_2$ | m11 | Thiourea | | |
| c12 | Pd/CaCO$_3$ | m12 | Na$_2$S$_2$O$_3$—xH$_2$O | | |
| c13 | Pd/C-diphenylsulfide | m13 | Na$_2$S | | |
| c14 | Pd/BaSO$_4$ | m14 | Chinoline | | |
| c15 | Pd(II)acetate-Polymethylhydrosiloxane | m15 | PPh$_3$ | | |

TABLE 1-continued

| Ref. | Catalyst | Ref. | Modifier | Ref. | Acid |
|---|---|---|---|---|---|
| c16 | Pd (Fe)/C | m16 | Mo(CO)$_6$ | | |
| c17 | Pd/C 5% sulfur | m17 | V(V) oxide | | |
| c18 | 5% Pd/0.5% V | m18 | V(IV) oxide | | |
| c19 | Pd/Pt | m19 | V(III) sulfide | | |
| | | m20 | NH$_4$VO$_3$ | | |
| | | m21 | ZnBr$_2$ | | |
| | | m22 | ZnCl$_2$ | | |
| | | m23 | MgBr$_2$ | | |
| | | m24 | MgO | | |
| | | m25 | FeCl$_2$ | | |
| | | m26 | FeCl$_3$ | | |
| | | m27 | Fe(OAc)$_2$) | | |
| | | m28 | n-Tetramethylammonium iodide | | |
| | | m29 | n-Tetraethylammonium iodide | | |
| | | m30 | n-Tetrabutylammonium iodide | | |
| | | m31 | n-Tetramethylammonium bromide (TMAB) | | |
| | | m32 | n-Tetraethylammonium bromide | | |
| | | m33 | n-Tetrabutylammoniumbromide (TBAB) | | |
| | | m34 | n-Tetramethylammonium chloride | | |
| | | m35 | n-Tetraethylammonium chloride | | |
| | | m36 | n-Tetrabutylammoniumchloride | | |
| | | m37 | NaCl | | |
| | | m38 | NaBr | | |
| | | m39 | NaI | | |
| | | m40 | KCl | | |
| | | m41 | KBr | | |
| | | m42 | KI | | |
| | | m43 | LiBr | | |
| | | m44 | MgBr$_2$ | | |
| | | m45 | AlCl$_3$ | | |
| | | m46 | CeCl$_3$ | | |
| | | m47 | CuCl | | |
| | | m48 | CuBr | | |
| | | m49 | CuI | | |
| | | m50 | CuBr$_2$ | | |
| | | m51 | BaSO$_4$ | | | c1+m1+a1, c1+m2+a1, c1+m3+a1, c1+m4+a1, c1+m5+a1, c1+m6+a1, c1+m7+a1, c1+m8+a1, c1+m9+a1, c1+m10+a1, c1+m11+a1, c1+m12+a1, c1+m13+a1, c1+m14+a1, c1+m15+a1, c1+m16+a1, c1+m17+a1, c1+m18+a1, c1+m19+a1, c1+m20+a1, c1+m21+a1, c1+m22+a1, c1+m23+a1, c1+m24+a1, c1+m25+a1, c1+m26+a1, c1+m27+a1, c1+m28+a1, c1+m29+a1, c1+m30+a1, c1+m31+a1, c1+m32+a1, c1+m33+a1, c1+m34+a1, c1+m35+a1, c1+m36+a1, c1+m37+a1, c1+m38+a1, c1+m39+a1, c1+m40+a1, c1+m41+a1, c1+m42+a1, c1+m43+a1, c1+m44+a1, c1+m45+a1, c1+m46+a1, c1+m47+a1, c1+m48+a1, c1+m49+a1, c1+m50+a1, c1+m51+a1, c1+m1+a2, c1+m2+a2, c1+m3+a2, c1+m4+a2, c1+m5+a2, c1+m6+a2, c1+m7+a2, c1+m8+a2, c1+m9+a2, c1+m10+a2, c1+m11+a2, c1+m12+a2, c1+m13+a2, c1+m14+a2, c1+m15+a2, c1+m16+a2, c1+m17+a2, c1+m18+a2, c1+m19+a2, c1+m20+a2, c1+m21+a2, c1+m22+a2, c1+m23+a2, c1+m24+a2, c1+m25+a2, c1+m26+a2, c1+m27+a2, c1+m28+a2, c1+m29+a2, c1+m30+a2, c1+m31+a2, c1+m32+a2, c1+m33+a2, c1+m34+a2, c1+m35+a2, c1+m36+a2, c1+m37+a2, c1+m38+a2, c1+m39+a2, c1+m40+a2, c1+m41+a2, c1+m42+a2, c1+m43+a2, c1+m44+a2, c1+m45+a2, c1+m46+a2, c1+m47+a2, c1+m48+a2, c1+m49+a2, c1+m50+a2, c1+m51+a2, c1+m1+a3, c1+m2+a3, c1+m3+a3, c1+m4+a3, c1+m5+a3, c1+m6+a3, c1+m7+a3, c1+m8+a3, c1+m9+a3, c1+m10+a3, c1+m11+a3, c1+m12+a3, c1+m13+a3, c1+m14+a3, c1+m15+a3, c1+m16+a3, c1+m17+a3, c1+m18+a3, c1+m19+a3, c1+m20+a3, c1+m21+a3, c1+m22+a3, c1+m23+a3, c1+m24+a3, c1+m25+a3, c1+m26+a3, c1+m27+a3, c1+m28+a3, c1+m29+a3, c1+m30+a3, c1+m31+a3, c1+m32+a3, c1+m33+a3, c1+m34+a3, c1+m35+a3, c1+m36+a3, c1+m37+a3, c1+m38+a3, c1+m39+a3, c1+m40+a3, c1+m41+a3, c1+m42+a3, c1+m43+a3, c1+m44+a3, c1+m45+a3, c1+m46+a3, c1+m47+a3, c1+m48+a3, c1+m49+a3, c1+m50+a3, c1+m51+a3, c1+m1+a4, c1+m2+a4, c1+m3+a4, c1+m4+a4, c1+m5+a4, c1+m6+a4, c1+m7+a4, c1+m8+a4, c1+m9+a4, c1+m10+a4, c1+m11+a4, c1+m12+a4, c1+m13+a4, c1+m14+a4, c1+m15+a4, c1+m16+a4, c1+m17+a4, c1+m18+a4, c1+m19+a4, c1+m20+a4, c1+m21+a4, c1+m22+a4, c1+m23+a4, c1+m24+a4, c1+m25+a4, c1+m26+a4, c1+m27+a4, c1+m28+a4, c1+m29+a4, c1+m30+a4, c1+m31+a4, c1+m32+a4, c1+m33+a4, c1+m34+a4, c1+m35+a4, c1+m36+a4, c1+m37+a4, c1+m38+a4, c1+m39+a4, c1+m40+a4, c1+m41+a4, c1+m42+a4, c1+m43+a4, c1+m44+a4, c1+m45+a4, c1+m46+a4, c1+m47+a4, c1+m48+a4, c1+m49+a4, c1+m50+a4, c1+m51+a4, c2+m1+a1, c2+m2+a1, c2+m3+a1, c2+m4+a1, c2+m5+a1, c2+m6+a1, c2+m7+a1, c2+m8+a1, c2+m9+a1, c2+m10+a1, c2+m11+a1, c2+m12+a1, c2+m13+a1, c2+m14+a1, c2+m15+a1, c2+m16+a1, c2+m17+a1, c2+m18+a1, c2+m19+a1, c2+m20+a1, c2+m21+a1, c2+m22+a1, c2+m23+a1, c2+m24+a1, c2+m25+a1, c2+m26+a1, c2+m27+a1, c2+m28+a1, c2+m29+a1, c2+m30+a1, c2+m31+a1, c2+m32+a1, c2+m33+a1, c2+m34+a1, c2+m35+a1, c2+m36+a1, c2+m37+a1, c2+m38+a1, c2+m39+a1, c2+m40+a1, c2+m41+a1, c2+m42+a1, c2+m43+a1, c2+m44+a1, c2+m45+a1, c2+m46+a1, c2+m47+a1, c2+m48+a1, c2+m49+a1, c2+m50+a1, c2+m51+a1, c2+m1+a2, c2+m2+a2, c2+m3+a2, c2+m4+a2, c2+m5+a2, c2+m6+a2, c2+m7+a2, c2+m8+a2, c2+m9+a2, c2+m10+a2, c2+m11+a2, c2+m12+a2, c2+m13+a2, c2+m14+a2, c2+m15+a2, c2+m16+a2, c2+m17+a2,
c2+m18+a2, c2+m19+a2, c2+m20+a2, c2+m21+a2,
c2+m22+a2, c2+m23+a2, c2+m24+a2, c2+m25+a2,
c2+m26+a2, c2+m27+a2, c2+m28+a2, c2+m29+a2,
c2+m30+a2, c2+m31+a2, c2+m32+a2, c2+m33+a2,
c2+m34+a2, c2+m35+a2, c2+m36+a2, c2+m37+a2,
c2+m38+a2, c2+m39+a2, c2+m40+a2, c2+m41+a2,
c2+m42+a2, c2+m43+a2, c2+m44+a2, c2+m45+a2,
c2+m46+a2, c2+m47+a2, c2+m48+a2, c2+m49+a2,
c2+m50+a2, c2+m51+a2, c2+m1+a3, c2+m2+a3, c2+m3+a3,
c2+m4+a3, c2+m5+a3, c2+m6+a3, c2+m7+a3, c2+m8+a3,
c2+m9+a3, c2+m10+a3, c2+m11+a3, c2+m12+a3,
c2+m13+a3, c2+m14+a3, c2+m15+a3, c2+m16+a3,
c2+m17+a3, c2+m18+a3, c2+m19+a3, c2+m20+a3,
c2+m21+a3, c2+m22+a3, c2+m23+a3, c2+m24+a3,
c2+m25+a3, c2+m26+a3, c2+m27+a3, c2+m28+a3,
c2+m29+a3, c2+m30+a3, c2+m31+a3, c2+m32+a3,
c2+m33+a3, c2+m34+a3, c2+m35+a3, c2+m36+a3,
c2+m37+a3, c2+m38+a3, c2+m39+a3, c2+m40+a3,
c2+m41+a3, c2+m42+a3, c2+m43+a3, c2+m44+a3,
c2+m45+a3, c2+m46+a3, c2+m47+a3, c2+m48+a3,
c2+m49+a3, c2+m50+a3, c2+m51+a3, c2+m1+a4, c2+m2+a4,
c2+m3+a4, c2+m4+a4, c2+m5+a4, c2+m6+a4, c2+m7+a4,
c2+m8+a4, c2+m9+a4, c2+m10+a4, c2+m11+a4,
c2+m12+a4, c2+m13+a4, c2+m14+a4, c2+m15+a4,
c2+m16+a4, c2+m17+a4, c2+m18+a4, c2+m19+a4,
c2+m20+a4, c2+m21+a4, c2+m22+a4, c2+m23+a4,
c2+m24+a4, c2+m25+a4, c2+m26+a4, c2+m27+a4,
c2+m28+a4, c2+m29+a4, c2+m30+a4, c2+m31+a4,
c2+m32+a4, c2+m33+a4, c2+m34+a4, c2+m35+a4,
c2+m36+a4, c2+m37+a4, c2+m38+a4, c2+m39+a4,
c2+m40+a4, c2+m41+a4, c2+m42+a4, c2+m43+a4,
c2+m44+a4, c2+m45+a4, c2+m46+a4, c2+m47+a4,
c2+m48+a4, c2+m49+a4, c2+m50+a4, c2+m51+a4,
c3+m1+a1, c3+m2+a1, c3+m3+a1, c3+m4+a1, c3+m5+a1,
c3+m6+a1, c3+m7+a1, c3+m8+a1, c3+m9+a1, c3+m10+a1,
c3+m11+a1, c3+m12+a1, c3+m13+a1, c3+m14+a1,
c3+m15+a1, c3+m16+a1, c3+m17+a1, c3+m18+a1,
c3+m19+a1, c3+m20+a1, c3+m21+a1, c3+m22+a1,
c3+m23+a1, c3+m24+a1, c3+m25+a1, c3+m26+a1,
c3+m27+a1, c3+m28+a1, c3+m29+a1, c3+m30+a1,
c3+m31+a1, c3+m32+a1, c3+m33+a1, c3+m34+a1,
c3+m35+a1, c3+m36+a1, c3+m37+a1, c3+m38+a1,
c3+m39+a1, c3+m40+a1, c3+m41+a1, c3+m42+a1,
c3+m43+a1, c3+m44+a1, c3+m45+a1, c3+m46+a1,
c3+m47+a1, c3+m48+a1, c3+m49+a1, c3+m50+a1,
c3+m51+a1, c3+m1+a2, c3+m2+a2, c3+m3+a2, c3+m4+a2,
c3+m5+a2, c3+m6+a2, c3+m7+a2, c3+m8+a2, c3+m9+a2,
c3+m10+a2, c3+m11+a2, c3+m12+a2, c3+m13+a2,
c3+m14+a2, c3+m15+a2, c3+m16+a2, c3+m17+a2,
c3+m18+a2, c3+m19+a2, c3+m20+a2, c3+m21+a2,
c3+m22+a2, c3+m23+a2, c3+m24+a2, c3+m25+a2,
c3+m26+a2, c3+m27+a2, c3+m28+a2, c3+m29+a2,
c3+m30+a2, c3+m31+a2, c3+m32+a2, c3+m33+a2,
c3+m34+a2, c3+m35+a2, c3+m36+a2, c3+m37+a2,
c3+m38+a2, c3+m39+a2, c3+m40+a2, c3+m41+a2,
c3+m42+a2, c3+m43+a2, c3+m44+a2, c3+m45+a2,
c3+m46+a2, c3+m47+a2, c3+m48+a2, c3+m49+a2,
c3+m50+a2, c3+m51+a2, c3+m1+a3, c3+m2+a3, c3+m3+a3,
c3+m4+a3, c3+m5+a3, c3+m6+a3, c3+m7+a3, c3+m8+a3,
c3+m9+a3, c3+m10+a3, c3+m11+a3, c3+m12+a3,
c3+m13+a3, c3+m14+a3, c3+m15+a3, c3+m16+a3,
c3+m17+a3, c3+m18+a3, c3+m19+a3, c3+m20+a3,
c3+m21+a3, c3+m22+a3, c3+m23+a3, c3+m24+a3,
c3+m25+a3, c3+m26+a3, c3+m27+a3, c3+m28+a3,
c3+m29+a3, c3+m30+a3, c3+m31+a3, c3+m32+a3,
c3+m33+a3, c3+m34+a3, c3+m35+a3, c3+m36+a3,
c3+m37+a3, c3+m38+a3, c3+m39+a3, c3+m40+a3,
c3+m41+a3, c3+m42+a3, c3+m43+a3, c3+m44+a3,
c3+m45+a3, c3+m46+a3, c3+m47+a3, c3+m48+a3,
c3+m49+a3, c3+m50+a3, c3+m51+a3, c3+m1+a4, c3+m2+a4,
c3+m3+a4, c3+m4+a4, c3+m5+a4, c3+m6+a4, c3+m7+a4,
c3+m8+a4, c3+m9+a4, c3+m10+a4, c3+m11+a4,
c3+m12+a4, c3+m13+a4, c3+m14+a4, c3+m15+a4,
c3+m16+a4, c3+m17+a4, c3+m18+a4, c3+m19+a4,
c3+m20+a4, c3+m21+a4, c3+m22+a4, c3+m23+a4,
c3+m24+a4, c3+m25+a4, c3+m26+a4, c3+m27+a4,
c3+m28+a4, c3+m29+a4, c3+m30+a4, c3+m31+a4,
c3+m32+a4, c3+m33+a4, c3+m34+a4, c3+m35+a4,
c3+m36+a4, c3+m37+a4, c3+m38+a4, c3+m39+a4,
c3+m40+a4, c3+m41+a4, c3+m42+a4, c3+m43+a4,
c3+m44+a4, c3+m45+a4, c3+m46+a4, c3+m47+a4,
c3+m48+a4, c3+m49+a4, c3+m50+a4, c3+m51+a4,
c4+m1+a1, c4+m2+a1, c4+m3+a1, c4+m4+a1, c4+m5+a1,
c4+m6+a1, c4+m7+a1, c4+m8+a1, c4+m9+a1, c4+m10+a1,
c4+m11+a1, c4+m12+a1, c4+m13+a1, c4+m14+a1,
c4+m15+a1, c4+m16+a1, c4+m17+a1, c4+m18+a1,
c4+m19+a1, c4+m20+a1, c4+m21+a1, c4+m22+a1,
c4+m23+a1, c4+m24+a1, c4+m25+a1, c4+m26+a1,
c4+m27+a1, c4+m28+a1, c4+m29+a1, c4+m30+a1,
c4+m31+a1, c4+m32+a1, c4+m33+a1, c4+m34+a1,
c4+m35+a1, c4+m36+a1, c4+m37+a1, c4+m38+a1,
c4+m39+a1, c4+m40+a1, c4+m41+a1, c4+m42+a1,
c4+m43+a1, c4+m44+a1, c4+m45+a1, c4+m46+a1,
c4+m47+a1, c4+m48+a1, c4+m49+a1, c4+m50+a1,
c4+m51+a1, c4+m1+a2, c4+m2+a2, c4+m3+a2, c4+m4+a2,
c4+m5+a2, c4+m6+a2, c4+m7+a2, c4+m8+a2, c4+m9+a2,
c4+m10+a2, c4+m11+a2, c4+m12+a2, c4+m13+a2,
c4+m14+a2, c4+m15+a2, c4+m16+a2, c4+m17+a2,
c4+m18+a2, c4+m19+a2, c4+m20+a2, c4+m21+a2,
c4+m22+a2, c4+m23+a2, c4+m24+a2, c4+m25+a2,
c4+m26+a2, c4+m27+a2, c4+m28+a2, c4+m29+a2,
c4+m30+a2, c4+m31+a2, c4+m32+a2, c4+m33+a2,
c4+m34+a2, c4+m35+a2, c4+m36+a2, c4+m37+a2,
c4+m38+a2, c4+m39+a2, c4+m40+a2, c4+m41+a2,
c4+m42+a2, c4+m43+a2, c4+m44+a2, c4+m45+a2,
c4+m46+a2, c4+m47+a2, c4+m48+a2, c4+m49+a2,
c4+m50+a2, c4+m51+a2, c4+m1+a3, c4+m2+a3, c4+m3+a3,
c4+m4+a3, c4+m5+a3, c4+m6+a3, c4+m7+a3, c4+m8+a3,
c4+m9+a3, c4+m10+a3, c4+m11+a3, c4+m12+a3,
c4+m13+a3, c4+m14+a3, c4+m15+a3, c4+m16+a3,
c4+m17+a3, c4+m18+a3, c4+m19+a3, c4+m20+a3,
c4+m21+a3, c4+m22+a3, c4+m23+a3, c4+m24+a3,
c4+m25+a3, c4+m26+a3, c4+m27+a3, c4+m28+a3,
c4+m29+a3, c4+m30+a3, c4+m31+a3, c4+m32+a3,
c4+m33+a3, c4+m34+a3, c4+m35+a3, c4+m36+a3,
c4+m37+a3, c4+m38+a3, c4+m39+a3, c4+m40+a3,
c4+m41+a3, c4+m42+a3, c4+m43+a3, c4+m44+a3,
c4+m45+a3, c4+m46+a3, c4+m47+a3, c4+m48+a3,
c4+m49+a3, c4+m50+a3, c4+m51+a3, c4+m1+a4, c4+m2+a4,
c4+m3+a4, c4+m4+a4, c4+m5+a4, c4+m6+a4, c4+m7+a4,
c4+m8+a4, c4+m9+a4, c4+m10+a4, c4+m11+a4,
c4+m12+a4, c4+m13+a4, c4+m14+a4, c4+m15+a4,
c4+m16+a4, c4+m17+a4, c4+m18+a4, c4+m19+a4,
c4+m20+a4, c4+m21+a4, c4+m22+a4, c4+m23+a4,
c4+m24+a4, c4+m25+a4, c4+m26+a4, c4+m27+a4,
c4+m28+a4, c4+m29+a4, c4+m30+a4, c4+m31+a4,
c4+m32+a4, c4+m33+a4, c4+m34+a4, c4+m35+a4,
c4+m36+a4, c4+m37+a4, c4+m38+a4, c4+m39+a4,
c4+m40+a4, c4+m41+a4, c4+m42+a4, c4+m43+a4,
c4+m44+a4, c4+m45+a4, c4+m46+a4, c4+m47+a4,
c4+m48+a4, c4+m49+a4, c4+m50+a4, c4+m51+a4,
c5+m1+a1, c5+m2+a1, c5+m3+a1, c5+m4+a1, c5+m5+a1,
c5+m6+a1, c5+m7+a1, c5+m8+a1, c5+m9+a1, c5+m10+a1, c5+m11+a1, c5+m12+a1, c5+m13+a1, c5+m14+a1,
c5+m15+a1, c5+m16+a1, c5+m17+a1, c5+m18+a1,
c5+m19+a1, c5+m20+a1, c5+m21+a1, c5+m22+a1,
c5+m23+a1, c5+m24+a1, c5+m25+a1, c5+m26+a1,
c5+m27+a1, c5+m28+a1, c5+m29+a1, c5+m30+a1,
c5+m31+a1, c5+m32+a1, c5+m33+a1, c5+m34+a1,
c5+m35+a1, c5+m36+a1, c5+m37+a1, c5+m38+a1,
c5+m39+a1, c5+m40+a1, c5+m41+a1, c5+m42+a1,
c5+m43+a1, c5+m44+a1, c5+m45+a1, c5+m46+a1,
c5+m47+a1, c5+m48+a1, c5+m49+a1, c5+m50+a1,
c5+m51+a1, c5+m1+a2, c5+m2+a2, c5+m3+a2, c5+m4+a2,
c5+m5+a2, c5+m6+a2, c5+m7+a2, c5+m8+a2, c5+m9+a2,
c5+m10+a2, c5+m11+a2, c5+m12+a2, c5+m13+a2,
c5+m14+a2, c5+m15+a2, c5+m16+a2, c5+m17+a2,
c5+m18+a2, c5+m19+a2, c5+m20+a2, c5+m21+a2,
c5+m22+a2, c5+m23+a2, c5+m24+a2, c5+m25+a2,
c5+m26+a2, c5+m27+a2, c5+m28+a2, c5+m29+a2,
c5+m30+a2, c5+m31+a2, c5+m32+a2, c5+m33+a2,
c5+m34+a2, c5+m35+a2, c5+m36+a2, c5+m37+a2,
c5+m38+a2, c5+m39+a2, c5+m40+a2, c5+m41+a2,
c5+m42+a2, c5+m43+a2, c5+m44+a2, c5+m45+a2,
c5+m46+a2, c5+m47+a2, c5+m48+a2, c5+m49+a2,
c5+m50+a2, c5+m51+a2, c5+m1+a3, c5+m2+a3, c5+m3+
a3, c5+m4+a3, c5+m5+a3, c5+m6+a3, c5+m7+a3, c5+m8+
a3, c5+m9+a3, c5+m10+a3, c5+m11+a3, c5+m12+a3,
c5+m13+a3, c5+m14+a3, c5+m15+a3, c5+m16+a3,
c5+m17+a3, c5+m18+a3, c5+m19+a3, c5+m20+a3,
c5+m21+a3, c5+m22+a3, c5+m23+a3, c5+m24+a3,
c5+m25+a3, c5+m26+a3, c5+m27+a3, c5+m28+a3,
c5+m29+a3, c5+m30+a3, c5+m31+a3, c5+m32+a3,
c5+m33+a3, c5+m34+a3, c5+m35+a3, c5+m36+a3,
c5+m37+a3, c5+m38+a3, c5+m39+a3, c5+m40+a3,
c5+m41+a3, c5+m42+a3, c5+m43+a3, c5+m44+a3,
c5+m45+a3, c5+m46+a3, c5+m47+a3, c5+m48+a3,
c5+m49+a3, c5+m50+a3, c5+m51+a3, c5+m1+a4, c5+m2+
a4, c5+m3+a4, c5+m4+a4, c5+m5+a4, c5+m6+a4, c5+m7+
a4, c5+m8+a4, c5+m9+a4, c5+m10+a4, c5+m11+a4,
c5+m12+a4, c5+m13+a4, c5+m14+a4, c5+m15+a4,
c5+m16+a4, c5+m17+a4, c5+m18+a4, c5+m19+a4,
c5+m20+a4, c5+m21+a4, c5+m22+a4, c5+m23+a4,
c5+m24+a4, c5+m25+a4, c5+m26+a4, c5+m27+a4,
c5+m28+a4, c5+m29+a4, c5+m30+a4, c5+m31+a4,
c5+m32+a4, c5+m33+a4, c5+m34+a4, c5+m35+a4,
c5+m36+a4, c5+m37+a4, c5+m38+a4, c5+m39+a4,
c5+m40+a4, c5+m41+a4, c5+m42+a4, c5+m43+a4,
c5+m44+a4, c5+m45+a4, c5+m46+a4, c5+m47+a4,
c5+m48+a4, c5+m49+a4, c5+m50+a4, c5+m51+a4,
c6+m1+a1, c6+m2+a1, c6+m3+a1, c6+m4+a1, c6+m5+a1,
c6+m6+a1, c6+m7+a1, c6+m8+a1, c6+m9+a1, c6+m10+a1,
c6+m11+a1, c6+m12+a1, c6+m13+a1, c6+m14+a1,
c6+m15+a1, c6+m16+a1, c6+m17+a1, c6+m18+a1,
c6+m19+a1, c6+m20+a1, c6+m21+a1, c6+m22+a1,
c6+m23+a1, c6+m24+a1, c6+m25+a1, c6+m26+a1,
c6+m27+a1, c6+m28+a1, c6+m29+a1, c6+m30+a1,
c6+m31+a1, c6+m32+a1, c6+m33+a1, c6+m34+a1,
c6+m35+a1, c6+m36+a1, c6+m37+a1, c6+m38+a1,
c6+m39+a1, c6+m40+a1, c6+m41+a1, c6+m42+a1,
c6+m43+a1, c6+m44+a1, c6+m45+a1, c6+m46+a1,
c6+m47+a1, c6+m48+a1, c6+m49+a1, c6+m50+a1,
c6+m51+a1, c6+m1+a2, c6+m2+a2, c6+m3+a2, c6+m4+a2,
c6+m5+a2, c6+m6+a2, c6+m7+a2, c6+m8+a2, c6+m9+a2,
c6+m10+a2, c6+m11+a2, c6+m12+a2, c6+m13+a2,
c6+m14+a2, c6+m15+a2, c6+m16+a2, c6+m17+a2,
c6+m18+a2, c6+m19+a2, c6+m20+a2, c6+m21+a2,
c6+m22+a2, c6+m23+a2, c6+m24+a2, c6+m25+a2,
c6+m26+a2, c6+m27+a2, c6+m28+a2, c6+m29+a2,
c6+m30+a2, c6+m31+a2, c6+m32+a2, c6+m33+a2,
c6+m34+a2, c6+m35+a2, c6+m36+a2, c6+m37+a2,
c6+m38+a2, c6+m39+a2, c6+m40+a2, c6+m41+a2,
c6+m42+a2, c6+m43+a2, c6+m44+a2, c6+m45+a2,
c6+m46+a2, c6+m47+a2, c6+m48+a2, c6+m49+a2,
c6+m50+a2, c6+m51+a2, c6+m1+a3, c6+m2+a3, c6+m3+
a3, c6+m4+a3, c6+m5+a3, c6+m6+a3, c6+m7+a3, c6+m8+
a3, c6+m9+a3, c6+m10+a3, c6+m11+a3, c6+m12+a3,
c6+m13+a3, c6+m14+a3, c6+m15+a3, c6+m16+a3,
c6+m17+a3, c6+m18+a3, c6+m19+a3, c6+m20+a3,
c6+m21+a3, c6+m22+a3, c6+m23+a3, c6+m24+a3,
c6+m25+a3, c6+m26+a3, c6+m27+a3, c6+m28+a3,
c6+m29+a3, c6+m30+a3, c6+m31+a3, c6+m32+a3,
c6+m33+a3, c6+m34+a3, c6+m35+a3, c6+m36+a3,
c6+m37+a3, c6+m38+a3, c6+m39+a3, c6+m40+a3,
c6+m41+a3, c6+m42+a3, c6+m43+a3, c6+m44+a3,
c6+m45+a3, c6+m46+a3, c6+m47+a3, c6+m48+a3,
c6+m49+a3, c6+m50+a3, c6+m51+a3, c6+m1+a4, c6+m2+
a4, c6+m3+a4, c6+m4+a4, c6+m5+a4, c6+m6+a4, c6+m7+
a4, c6+m8+a4, c6+m9+a4, c6+m10+a4, c6+m11+a4,
c6+m12+a4, c6+m13+a4, c6+m14+a4, c6+m15+a4,
c6+m16+a4, c6+m17+a4, c6+m18+a4, c6+m19+a4,
c6+m20+a4, c6+m21+a4, c6+m22+a4, c6+m23+a4,
c6+m24+a4, c6+m25+a4, c6+m26+a4, c6+m27+a4,
c6+m28+a4, c6+m29+a4, c6+m30+a4, c6+m31+a4,
c6+m32+a4, c6+m33+a4, c6+m34+a4, c6+m35+a4,
c6+m36+a4, c6+m37+a4, c6+m38+a4, c6+m39+a4,
c6+m40+a4, c6+m41+a4, c6+m42+a4, c6+m43+a4,
c6+m44+a4, c6+m45+a4, c6+m46+a4, c6+m47+a4,
c6+m48+a4, c6+m49+a4, c6+m50+a4, c6+m51+a4,
c7+m1+a1, c7+m2+a1, c7+m3+a1, c7+m4+a1, c7+m5+a1,
c7+m6+a1, c7+m7+a1, c7+m8+a1, c7+m9+a1, c7+m10+a1,
c7+m11+a1, c7+m12+a1, c7+m13+a1, c7+m14+a1,
c7+m15+a1, c7+m16+a1, c7+m17+a1, c7+m18+a1,
c7+m19+a1, c7+m20+a1, c7+m21+a1, c7+m22+a1,
c7+m23+a1, c7+m24+a1, c7+m25+a1, c7+m26+a1,
c7+m27+a1, c7+m28+a1, c7+m29+a1, c7+m30+a1,
c7+m31+a1, c7+m32+a1, c7+m33+a1, c7+m34+a1,
c7+m35+a1, c7+m36+a1, c7+m37+a1, c7+m38+a1,
c7+m39+a1, c7+m40+a1, c7+m41+a1, c7+m42+a1,
c7+m43+a1, c7+m44+a1, c7+m45+a1, c7+m46+a1,
c7+m47+a1, c7+m48+a1, c7+m49+a1, c7+m50+a1,
c7+m51+a1, c7+m1+a2, c7+m2+a2, c7+m3+a2, c7+m4+a2,
c7+m5+a2, c7+m6+a2, c7+m7+a2, c7+m8+a2, c7+m9+a2,
c7+m10+a2, c7+m11+a2, c7+m12+a2, c7+m13+a2,
c7+m14+a2, c7+m15+a2, c7+m16+a2, c7+m17+a2,
c7+m18+a2, c7+m19+a2, c7+m20+a2, c7+m21+a2,
c7+m22+a2, c7+m23+a2, c7+m24+a2, c7+m25+a2,
c7+m26+a2, c7+m27+a2, c7+m28+a2, c7+m29+a2,
c7+m30+a2, c7+m31+a2, c7+m32+a2, c7+m33+a2,
c7+m34+a2, c7+m35+a2, c7+m36+a2, c7+m37+a2,
c7+m38+a2, c7+m39+a2, c7+m40+a2, c7+m41+a2,
c7+m42+a2, c7+m43+a2, c7+m44+a2, c7+m45+a2,
c7+m46+a2, c7+m47+a2, c7+m48+a2, c7+m49+a2,
c7+m50+a2, c7+m51+a2, c7+m1+a3, c7+m2+a3, c7+m3+
a3, c7+m4+a3, c7+m5+a3, c7+m6+a3, c7+m7+a3, c7+m8+
a3, c7+m9+a3, c7+m10+a3, c7+m11+a3, c7+m12+a3,
c7+m13+a3, c7+m14+a3, c7+m15+a3, c7+m16+a3,
c7+m17+a3, c7+m18+a3, c7+m19+a3, c7+m20+a3,
c7+m21+a3, c7+m22+a3, c7+m23+a3, c7+m24+a3,
c7+m25+a3, c7+m26+a3, c7+m27+a3, c7+m28+a3,
c7+m29+a3, c7+m30+a3, c7+m31+a3, c7+m32+a3,
c7+m33+a3, c7+m34+a3, c7+m35+a3, c7+m36+a3,
c7+m37+a3, c7+m38+a3, c7+m39+a3, c7+m40+a3,
c7+m41+a3, c7+m42+a3, c7+m43+a3, c7+m44+a3,
c7+m45+a3, c7+m46+a3, c7+m47+a3, c7+m48+a3,
c7+m49+a3, c7+m50+a3, c7+m51+a3, c7+m1+a4, c7+m2+
a4, c7+m3+a4, c7+m4+a4, c7+m5+a4, c7+m6+a4, c7+m7+ a4, c7+m8+a4, c7+m9+a4, c7+m10+a4, c7+m11+a4, c7+m12+a4, c7+m13+a4, c7+m14+a4, c7+m15+a4, c7+m16+a4, c7+m17+a4, c7+m18+a4, c7+m19+a4, c7+m20+a4, c7+m21+a4, c7+m22+a4, c7+m23+a4, c7+m24+a4, c7+m25+a4, c7+m26+a4, c7+m27+a4, c7+m28+a4, c7+m29+a4, c7+m30+a4, c7+m31+a4, c7+m32+a4, c7+m33+a4, c7+m34+a4, c7+m35+a4, c7+m36+a4, c7+m37+a4, c7+m38+a4, c7+m39+a4, c7+m40+a4, c7+m41+a4, c7+m42+a4, c7+m43+a4, c7+m44+a4, c7+m45+a4, c7+m46+a4, c7+m47+a4, c7+m48+a4, c7+m49+a4, c7+m50+a4, c7+m51+a4, c8+m1+a1, c8+m2+a1, c8+m3+a1, c8+m4+a1, c8+m5+a1, c8+m6+a1, c8+m7+a1, c8+m8+a1, c8+m9+a1, c8+m10+a1, c8+m11+a1, c8+m12+a1, c8+m13+a1, c8+m14+a1, c8+m15+a1, c8+m16+a1, c8+m17+a1, c8+m18+a1, c8+m19+a1, c8+m20+a1, c8+m21+a1, c8+m22+a1, c8+m23+a1, c8+m24+a1, c8+m25+a1, c8+m26+a1, c8+m27+a1, c8+m28+a1, c8+m29+a1, c8+m30+a1, c8+m31+a1, c8+m32+a1, c8+m33+a1, c8+m34+a1, c8+m35+a1, c8+m36+a1, c8+m37+a1, c8+m38+a1, c8+m39+a1, c8+m40+a1, c8+m41+a1, c8+m42+a1, c8+m43+a1, c8+m44+a1, c8+m45+a1, c8+m46+a1, c8+m47+a1, c8+m48+a1, c8+m49+a1, c8+m50+a1, c8+m51+a1, c8+m1+a2, c8+m2+a2, c8+m3+a2, c8+m4+a2, c8+m5+a2, c8+m6+a2, c8+m7+a2, c8+m8+a2, c8+m9+a2, c8+m10+a2, c8+m11+a2, c8+m12+a2, c8+m13+a2, c8+m14+a2, c8+m15+a2, c8+m16+a2, c8+m17+a2, c8+m18+a2, c8+m19+a2, c8+m20+a2, c8+m21+a2, c8+m22+a2, c8+m23+a2, c8+m24+a2, c8+m25+a2, c8+m26+a2, c8+m27+a2, c8+m28+a2, c8+m29+a2, c8+m30+a2, c8+m31+a2, c8+m32+a2, c8+m33+a2, c8+m34+a2, c8+m35+a2, c8+m36+a2, c8+m37+a2, c8+m38+a2, c8+m39+a2, c8+m40+a2, c8+m41+a2, c8+m42+a2, c8+m43+a2, c8+m44+a2, c8+m45+a2, c8+m46+a2, c8+m47+a2, c8+m48+a2, c8+m49+a2, c8+m50+a2, c8+m51+a2, c8+m1+a3, c8+m2+a3, c8+m3+a3, c8+m4+a3, c8+m5+a3, c8+m6+a3, c8+m7+a3, c8+m8+a3, c8+m9+a3, c8+m10+a3, c8+m11+a3, c8+m12+a3, c8+m13+a3, c8+m14+a3, c8+m15+a3, c8+m16+a3, c8+m17+a3, c8+m18+a3, c8+m19+a3, c8+m20+a3, c8+m21+a3, c8+m22+a3, c8+m23+a3, c8+m24+a3, c8+m25+a3, c8+m26+a3, c8+m27+a3, c8+m28+a3, c8+m29+a3, c8+m30+a3, c8+m31+a3, c8+m32+a3, c8+m33+a3, c8+m34+a3, c8+m35+a3, c8+m36+a3, c8+m37+a3, c8+m38+a3, c8+m39+a3, c8+m40+a3, c8+m41+a3, c8+m42+a3, c8+m43+a3, c8+m44+a3, c8+m45+a3, c8+m46+a3, c8+m47+a3, c8+m48+a3, c8+m49+a3, c8+m50+a3, c8+m51+a3, c8+m1+a4, c8+m2+a4, c8+m3+a4, c8+m4+a4, c8+m5+a4, c8+m6+a4, c8+m7+a4, c8+m8+a4, c8+m9+a4, c8+m10+a4, c8+m11+a4, c8+m12+a4, c8+m13+a4, c8+m14+a4, c8+m15+a4, c8+m16+a4, c8+m17+a4, c8+m18+a4, c8+m19+a4, c8+m20+a4, c8+m21+a4, c8+m22+a4, c8+m23+a4, c8+m24+a4, c8+m25+a4, c8+m26+a4, c8+m27+a4, c8+m28+a4, c8+m29+a4, c8+m30+a4, c8+m31+a4, c8+m32+a4, c8+m33+a4, c8+m34+a4, c8+m35+a4, c8+m36+a4, c8+m37+a4, c8+m38+a4, c8+m39+a4, c8+m40+a4, c8+m41+a4, c8+m42+a4, c8+m43+a4, c8+m44+a4, c8+m45+a4, c8+m46+a4, c8+m47+a4, c8+m48+a4, c8+m49+a4, c8+m50+a4, c8+m51+a4, c9+m1+a1, c9+m2+a1, c9+m3+a1, c9+m4+a1, c9+m5+a1, c9+m6+a1, c9+m7+a1, c9+m8+a1, c9+m9+a1, c9+m10+a1, c9+m11+a1, c9+m12+a1, c9+m13+a1, c9+m14+a1, c9+m15+a1, c9+m16+a1, c9+m17+a1, c9+m18+a1, c9+m19+a1, c9+m20+a1, c9+m21+a1, c9+m22+a1, c9+m23+a1, c9+m24+a1, c9+m25+a1, c9+m26+a1, c9+m27+a1, c9+m28+a1, c9+m29+a1, c9+m30+a1, c9+m31+a1, c9+m32+a1, c9+m33+a1, c9+m34+a1, c9+m35+a1, c9+m36+a1, c9+m37+a1, c9+m38+a1, c9+m39+a1, c9+m40+a1, c9+m41+a1, c9+m42+a1, c9+m43+a1, c9+m44+a1, c9+m45+a1, c9+m46+a1, c9+m47+a1, c9+m48+a1, c9+m49+a1, c9+m50+a1, c9+m51+a1, c9+m1+a2, c9+m2+a2, c9+m3+a2, c9+m4+a2, c9+m5+a2, c9+m6+a2, c9+m7+a2, c9+m8+a2, c9+m9+a2, c9+m10+a2, c9+m11+a2, c9+m12+a2, c9+m13+a2, c9+m14+a2, c9+m15+a2, c9+m16+a2, c9+m17+a2, c9+m18+a2, c9+m19+a2, c9+m20+a2, c9+m21+a2, c9+m22+a2, c9+m23+a2, c9+m24+a2, c9+m25+a2, c9+m26+a2, c9+m27+a2, c9+m28+a2, c9+m29+a2, c9+m30+a2, c9+m31+a2, c9+m32+a2, c9+m33+a2, c9+m34+a2, c9+m35+a2, c9+m36+a2, c9+m37+a2, c9+m38+a2, c9+m39+a2, c9+m40+a2, c9+m41+a2, c9+m42+a2, c9+m43+a2, c9+m44+a2, c9+m45+a2, c9+m46+a2, c9+m47+a2, c9+m48+a2, c9+m49+a2, c9+m50+a2, c9+m51+a2, c9+m1+a3, c9+m2+a3, c9+m3+a3, c9+m4+a3, c9+m5+a3, c9+m6+a3, c9+m7+a3, c9+m8+a3, c9+m9+a3, c9+m10+a3, c9+m11+a3, c9+m12+a3, c9+m13+a3, c9+m14+a3, c9+m15+a3, c9+m16+a3, c9+m17+a3, c9+m18+a3, c9+m19+a3, c9+m20+a3, c9+m21+a3, c9+m22+a3, c9+m23+a3, c9+m24+a3, c9+m25+a3, c9+m26+a3, c9+m27+a3, c9+m28+a3, c9+m29+a3, c9+m30+a3, c9+m31+a3, c9+m32+a3, c9+m33+a3, c9+m34+a3, c9+m35+a3, c9+m36+a3, c9+m37+a3, c9+m38+a3, c9+m39+a3, c9+m40+a3, c9+m41+a3, c9+m42+a3, c9+m43+a3, c9+m44+a3, c9+m45+a3, c9+m46+a3, c9+m47+a3, c9+m48+a3, c9+m49+a3, c9+m50+a3, c9+m51+a3, c9+m1+a4, c9+m2+a4, c9+m3+a4, c9+m4+a4, c9+m5+a4, c9+m6+a4, c9+m7+a4, c9+m8+a4, c9+m9+a4, c9+m10+a4, c9+m11+a4, c9+m12+a4, c9+m13+a4, c9+m14+a4, c9+m15+a4, c9+m16+a4, c9+m17+a4, c9+m18+a4, c9+m19+a4, c9+m20+a4, c9+m21+a4, c9+m22+a4, c9+m23+a4, c9+m24+a4, c9+m25+a4, c9+m26+a4, c9+m27+a4, c9+m28+a4, c9+m29+a4, c9+m30+a4, c9+m31+a4, c9+m32+a4, c9+m33+a4, c9+m34+a4, c9+m35+a4, c9+m36+a4, c9+m37+a4, c9+m38+a4, c9+m39+a4, c9+m40+a4, c9+m41+a4, c9+m42+a4, c9+m43+a4, c9+m44+a4, c9+m45+a4, c9+m46+a4, c9+m47+a4, c9+m48+a4, c9+m49+a4, c9+m50+a4, c9+m51+a4, c10+m1+a1, c10+m2+a1, c10+m3+a1, c10+m4+a1, c10+m5+a1, c10+m6+a1, c10+m7+a1, c10+m8+a1, c10+m9+a1, c10+m10+a1, c10+m11+a1, c10+m12+a1, c10+m13+a1, c10+m14+a1, c10+m15+a1, c10+m16+a1, c10+m17+a1, c10+m18+a1, c10+m19+a1, c10+m20+a1, c10+m21+a1, c10+m22+a1, c10+m23+a1, c10+m24+a1, c10+m25+a1, c10+m26+a1, c10+m27+a1, c10+m28+a1, c10+m29+a1, c10+m30+a1, c10+m31+a1, c10+m32+a1, c10+m33+a1, c10+m34+a1, c10+m35+a1, c10+m36+a1, c10+m37+a1, c10+m38+a1, c10+m39+a1, c10+m40+a1, c10+m41+a1, c10+m42+a1, c10+m43+a1, c10+m44+a1, c10+m45+a1, c10+m46+a1, c10+m47+a1, c10+m48+a1, c10+m49+a1, c10+m50+a1, c10+m51+a1, c10+m1+a2, c10+m2+a2, c10+m3+a2, c10+m4+a2, c10+m5+a2, c10+m6+a2, c10+m7+a2, c10+m8+a2, c10+m9+a2, c10+m10+a2, c10+m11+a2, c10+m12+a2, c10+m13+a2, c10+m14+a2, c10+m15+a2, c10+m16+a2, c10+m17+a2, c10+m18+a2, c10+m19+a2, c10+m20+a2, c10+m21+a2, c10+m22+a2, c10+m23+a2, c10+m24+a2, c10+m25+a2, c10+m26+a2, c10+m27+a2, c10+m28+a2, c10+m29+a2, c10+m30+a2, c10+m31+a2, c10+m32+a2, c10+m33+a2, c10+m34+a2, c10+m35+a2, c10+m36+a2, c10+m37+a2, c10+m38+a2, c10+m39+a2, c10+m40+a2, c10+m41+a2, c10+m42+a2, c10+m43+a2, c10+m44+a2, c10+m45+a2, c10+m46+a2, c10+m47+a2, c10+m48+a2, c10+m49+a2, c10+m50+a2, c10+m51+a2, c10+ m1+a3, c10+m2+a3, c10+m3+a3, c10+m4+a3, c10+m5+a3, c10+m6+a3, c10+m7+a3, c10+m8+a3, c10+m9+a3, c10+m10+a3, c10+m11+a3, c10+m12+a3, c10+m13+a3, c10+m14+a3, c10+m15+a3, c10+m16+a3, c10+m17+a3, c10+m18+a3, c10+m19+a3, c10+m20+a3, c10+m21+a3, c10+m22+a3, c10+m23+a3, c10+m24+a3, c10+m25+a3, c10+m26+a3, c10+m27+a3, c10+m28+a3, c10+m29+a3, c10+m30+a3, c10+m31+a3, c10+m32+a3, c10+m33+a3, c10+m34+a3, c10+m35+a3, c10+m36+a3, c10+m37+a3, c10+m38+a3, c10+m39+a3, c10+m40+a3, c10+m41+a3, c10+m42+a3, c10+m43+a3, c10+m44+a3, c10+m45+a3, c10+m46+a3, c10+m47+a3, c10+m48+a3, c10+m49+a3, c10+m50+a3, c10+m51+a3, c10+m1+a4, c10+m2+a4, c10+m3+a4, c10+m4+a4, c10+m5+a4, c10+m6+a4, c10+m7+a4, c10+m8+a4, c10+m9+a4, c10+m10+a4, c10+m11+a4, c10+m12+a4, c10+m13+a4, c10+m14+a4, c10+m15+a4, c10+m16+a4, c10+m17+a4, c10+m18+a4, c10+m19+a4, c10+m20+a4, c10+m21+a4, c10+m22+a4, c10+m23+a4, c10+m24+a4, c10+m25+a4, c10+m26+a4, c10+m27+a4, c10+m28+a4, c10+m29+a4, c10+m30+a4, c10+m31+a4, c10+m32+a4, c10+m33+a4, c10+m34+a4, c10+m35+a4, c10+m36+a4, c10+m37+a4, c10+m38+a4, c10+m39+a4, c10+m40+a4, c10+m41+a4, c10+m42+a4, c10+m43+a4, c10+m44+a4, c10+m45+a4, c10+m46+a4, c10+m47+a4, c10+m48+a4, c10+m49+a4, c10+m50+a4, c10+m51+a4, c11+m1+a1, c11+m2+a1, c11+m3+a1, c11+m4+a1, c11+m5+a1, c11+m6+a1, c11+m7+a1, c11+m8+a1, c11+m9+a1, c11+m10+a1, c11+m11+a1, c11+m12+a1, c11+m13+a1, c11+m14+a1, c11+m15+a1, c11+m16+a1, c11+m17+a1, c11+m18+a1, c11+m19+a1, c11+m20+a1, c11+m21+a1, c11+m22+a1, c11+m23+a1, c11+m24+a1, c11+m25+a1, c11+m26+a1, c11+m27+a1, c11+m28+a1, c11+m29+a1, c11+m30+a1, c11+m31+a1, c11+m32+a1, c11+m33+a1, c11+m34+a1, c11+m35+a1, c11+m36+a1, c11+m37+a1, c11+m38+a1, c11+m39+a1, c11+m40+a1, c11+m41+a1, c11+m42+a1, c11+m43+a1, c11+m44+a1, c11+m45+a1, c11+m46+a1, c11+m47+a1, c11+m48+a1, c11+m49+a1, c11+m50+a1, c11+m51+a1, c11+m1+a2, c11+m2+a2, c11+m3+a2, c11+m4+a2, c11+m5+a2, c11+m6+a2, c11+m7+a2, c11+m8+a2, c11+m9+a2, c11+m10+a2, c11+m11+a2, c11+m12+a2, c11+m13+a2, c11+m14+a2, c11+m15+a2, c11+m16+a2, c11+m17+a2, c11+m18+a2, c11+m19+a2, c11+m20+a2, c11+m21+a2, c11+m22+a2, c11+m23+a2, c11+m24+a2, c11+m25+a2, c11+m26+a2, c11+m27+a2, c11+m28+a2, c11+m29+a2, c11+m30+a2, c11+m31+a2, c11+m32+a2, c11+m33+a2, c11+m34+a2, c11+m35+a2, c11+m36+a2, c11+m37+a2, c11+m38+a2, c11+m39+a2, c11+m40+a2, c11+m41+a2, c11+m42+a2, c11+m43+a2, c11+m44+a2, c11+m45+a2, c11+m46+a2, c11+m47+a2, c11+m48+a2, c11+m49+a2, c11+m50+a2, c11+m51+a2, c11+m1+a3, c11+m2+a3, c11+m3+a3, c11+m4+a3, c11+m5+a3, c11+m6+a3, c11+m7+a3, c11+m8+a3, c11+m9+a3, c11+m10+a3, c11+m11+a3, c11+m12+a3, c11+m13+a3, c11+m14+a3, c11+m15+a3, c11+m16+a3, c11+m17+a3, c11+m18+a3, c11+m19+a3, c11+m20+a3, c11+m21+a3, c11+m22+a3, c11+m23+a3, c11+m24+a3, c11+m25+a3, c11+m26+a3, c11+m27+a3, c11+m28+a3, c11+m29+a3, c11+m30+a3, c11+m31+a3, c11+m32+a3, c11+m33+a3, c11+m34+a3, c11+m35+a3, c11+m36+a3, c11+m37+a3, c11+m38+a3, c11+m39+a3, c11+m40+a3, c11+m41+a3, c11+m42+a3, c11+m43+a3, c11+m44+a3, c11+m45+a3, c11+m46+a3, c11+m47+a3, c11+m48+a3, c11+m49+a3, c11+m50+a3, c11+m51+a3, c11+m1+a4, c11+m2+a4, c11+m3+a4, c11+m4+a4, c11+m5+a4, c11+m6+a4, c11+m7+a4, c11+m8+a4, c11+m9+a4, c11+m10+a4, c11+m11+a4, c11+m12+a4, c11+m13+a4, c11+m14+a4, c11+m15+a4, c11+m16+a4, c11+m17+a4, c11+m18+a4, c11+m19+a4, c11+m20+a4, c11+m21+a4, c11+m22+a4, c11+m23+a4, c11+m24+a4, c11+m25+a4, c11+m26+a4, c11+m27+a4, c11+m28+a4, c11+m29+a4, c11+m30+a4, c11+m31+a4, c11+m32+a4, c11+m33+a4, c11+m34+a4, c11+m35+a4, c11+m36+a4, c11+m37+a4, c11+m38+a4, c11+m39+a4, c11+m40+a4, c11+m41+a4, c11+m42+a4, c11+m43+a4, c11+m44+a4, c11+m45+a4, c11+m46+a4, c11+m47+a4, c11+m48+a4, c11+m49+a4, c11+m50+a4, c11+m51+a4, c12+m1+a1, c12+m2+a1, c12+m3+a1, c12+m4+a1, c12+m5+a1, c12+m6+a1, c12+m7+a1, c12+m8+a1, c12+m9+a1, c12+m10+a1, c12+m11+a1, c12+m12+a1, c12+m13+a1, c12+m14+a1, c12+m15+a1, c12+m16+a1, c12+m17+a1, c12+m18+a1, c12+m19+a1, c12+m20+a1, c12+m21+a1, c12+m22+a1, c12+m23+a1, c12+m24+a1, c12+m25+a1, c12+m26+a1, c12+m27+a1, c12+m28+a1, c12+m29+a1, c12+m30+a1, c12+m31+a1, c12+m32+a1, c12+m33+a1, c12+m34+a1, c12+m35+a1, c12+m36+a1, c12+m37+a1, c12+m38+a1, c12+m39+a1, c12+m40+a1, c12+m41+a1, c12+m42+a1, c12+m43+a1, c12+m44+a1, c12+m45+a1, c12+m46+a1, c12+m47+a1, c12+m48+a1, c12+m49+a1, c12+m50+a1, c12+m51+a1, c12+m1+a2, c12+m2+a2, c12+m3+a2, c12+m4+a2, c12+m5+a2, c12+m6+a2, c12+m7+a2, c12+m8+a2, c12+m9+a2, c12+m10+a2, c12+m11+a2, c12+m12+a2, c12+m13+a2, c12+m14+a2, c12+m15+a2, c12+m16+a2, c12+m17+a2, c12+m18+a2, c12+m19+a2, c12+m20+a2, c12+m21+a2, c12+m22+a2, c12+m23+a2, c12+m24+a2, c12+m25+a2, c12+m26+a2, c12+m27+a2, c12+m28+a2, c12+m29+a2, c12+m30+a2, c12+m31+a2, c12+m32+a2, c12+m33+a2, c12+m34+a2, c12+m35+a2, c12+m36+a2, c12+m37+a2, c12+m38+a2, c12+m39+a2, c12+m40+a2, c12+m41+a2, c12+m42+a2, c12+m43+a2, c12+m44+a2, c12+m45+a2, c12+m46+a2, c12+m47+a2, c12+m48+a2, c12+m49+a2, c12+m50+a2, c12+m51+a2, c12+m1+a3, c12+m2+a3, c12+m3+a3, c12+m4+a3, c12+m5+a3, c12+m6+a3, c12+m7+a3, c12+m8+a3, c12+m9+a3, c12+m10+a3, c12+m11+a3, c12+m12+a3, c12+m13+a3, c12+m14+a3, c12+m15+a3, c12+m16+a3, c12+m17+a3, c12+m18+a3, c12+m19+a3, c12+m20+a3, c12+m21+a3, c12+m22+a3, c12+m23+a3, c12+m24+a3, c12+m25+a3, c12+m26+a3, c12+m27+a3, c12+m28+a3, c12+m29+a3, c12+m30+a3, c12+m31+a3, c12+m32+a3, c12+m33+a3, c12+m34+a3, c12+m35+a3, c12+m36+a3, c12+m37+a3, c12+m38+a3, c12+m39+a3, c12+m40+a3, c12+m41+a3, c12+m42+a3, c12+m43+a3, c12+m44+a3, c12+m45+a3, c12+m46+a3, c12+m47+a3, c12+m48+a3, c12+m49+a3, c12+m50+a3, c12+m51+a3, c12+m1+a4, c12+m2+a4, c12+m3+a4, c12+m4+a4, c12+m5+a4, c12+m6+a4, c12+m7+a4, c12+m8+a4, c12+m9+a4, c12+m10+a4, c12+m11+a4, c12+m12+a4, c12+m13+a4, c12+m14+a4, c12+m15+a4, c12+m16+a4, c12+m17+a4, c12+m18+a4, c12+m19+a4, c12+m20+a4, c12+m21+a4, c12+m22+a4, c12+m23+a4, c12+m24+a4, c12+m25+a4, c12+m26+a4, c12+m27+a4, c12+m28+a4, c12+m29+a4, c12+m30+a4, c12+m31+a4, c12+m32+a4, c12+m33+a4, c12+m34+a4, c12+m35+a4, c12+m36+a4, c12+m37+a4, c12+m38+a4, c12+m39+a4, c12+m40+a4, c12+m41+a4, c12+m42+a4, c12+m43+a4, c12+m44+a4, c12+m45+a4, c12+m46+a4, c12+m47+a4, c12+m48+a4, c12+m49+a4, c12+m50+a4, c12+m51+a4, c13+m1+a1, c13+m2+a1, c13+m3+a1, c13+m4+a1, c13+m5+a1, c13+m6+a1, c13+m7+a1, c13+m8+a1, c13+m9+a1, c13+m10+a1, c13+m11+a1, c13+m12+a1, c13+m13+a1, c13+m14+a1, c13+m15+a1, c13+m16+a1, c13+m17+a1, c13+m18+a1, c13+m19+a1, c13+m20+a1, c13+m21+a1, c13+m22+a1, c13+m23+a1, c13+m24+a1, c13+m25+a1, c13+m26+a1, c13+m27+a1, c13+m28+a1, c13+m29+a1, c13+m30+a1, c13+m31+a1, c13+m32+a1, c13+m33+a1, c13+m34+a1, c13+m35+a1, c13+m36+a1, c13+m37+a1, c13+ m38+a1, c13+m39+a1, c13+m40+a1, c13+m41+a1, c13+m42+a1, c13+m43+a1, c13+m44+a1, c13+m45+a1, c13+m46+a1, c13+m47+a1, c13+m48+a1, c13+m49+a1, c13+m50+a1, c13+m51+a1, c13+m1+a2, c13+m2+a2, c13+m3+a2, c13+m4+a2, c13+m5+a2, c13+m6+a2, c13+m7+a2, c13+m8+a2, c13+m9+a2, c13+m10+a2, c13+m11+a2, c13+m12+a2, c13+m13+a2, c13+m14+a2, c13+m15+a2, c13+m16+a2, c13+m17+a2, c13+m18+a2, c13+m19+a2, c13+m20+a2, c13+m21+a2, c13+m22+a2, c13+m23+a2, c13+m24+a2, c13+m25+a2, c13+m26+a2, c13+m27+a2, c13+m28+a2, c13+m29+a2, c13+m30+a2, c13+m31+a2, c13+m32+a2, c13+m33+a2, c13+m34+a2, c13+m35+a2, c13+m36+a2, c13+m37+a2, c13+m38+a2, c13+m39+a2, c13+m40+a2, c13+m41+a2, c13+m42+a2, c13+m43+a2, c13+m44+a2, c13+m45+a2, c13+m46+a2, c13+m47+a2, c13+m48+a2, c13+m49+a2, c13+m50+a2, c13+m51+a2, c13+m1+a3, c13+m2+a3, c13+m3+a3, c13+m4+a3, c13+m5+a3, c13+m6+a3, c13+m7+a3, c13+m8+a3, c13+m9+a3, c13+m10+a3, c13+m11+a3, c13+m12+a3, c13+m13+a3, c13+m14+a3, c13+m15+a3, c13+m16+a3, c13+m17+a3, c13+m18+a3, c13+m19+a3, c13+m20+a3, c13+m21+a3, c13+m22+a3, c13+m23+a3, c13+m24+a3, c13+m25+a3, c13+m26+a3, c13+m27+a3, c13+m28+a3, c13+m29+a3, c13+m30+a3, c13+m31+a3, c13+m32+a3, c13+m33+a3, c13+m34+a3, c13+m35+a3, c13+m36+a3, c13+m37+a3, c13+m38+a3, c13+m39+a3, c13+m40+a3, c13+m41+a3, c13+m42+a3, c13+m43+a3, c13+m44+a3, c13+m45+a3, c13+m46+a3, c13+m47+a3, c13+m48+a3, c13+m49+a3, c13+m50+a3, c13+m51+a3, c13+m1+a4, c13+m2+a4, c13+m3+a4, c13+m4+a4, c13+m5+a4, c13+m6+a4, c13+m7+a4, c13+m8+a4, c13+m9+a4, c13+m10+a4, c13+m11+a4, c13+m12+a4, c13+m13+a4, c13+m14+a4, c13+m15+a4, c13+m16+a4, c13+m17+a4, c13+m18+a4, c13+m19+a4, c13+m20+a4, c13+m21+a4, c13+m22+a4, c13+m23+a4, c13+m24+a4, c13+m25+a4, c13+m26+a4, c13+m27+a4, c13+m28+a4, c13+m29+a4, c13+m30+a4, c13+m31+a4, c13+m32+a4, c13+m33+a4, c13+m34+a4, c13+m35+a4, c13+m36+a4, c13+m37+a4, c13+m38+a4, c13+m39+a4, c13+m40+a4, c13+m41+a4, c13+m42+a4, c13+m43+a4, c13+m44+a4, c13+m45+a4, c13+m46+a4, c13+m47+a4, c13+m48+a4, c13+m49+a4, c13+m50+a4, c13+m51+a4, c14+m1+a1, c14+m2+a1, c14+m3+a1, c14+m4+a1, c14+m5+a1, c14+m6+a1, c14+m7+a1, c14+m8+a1, c14+m9+a1, c14+m10+a1, c14+m11+a1, c14+m12+a1, c14+m13+a1, c14+m14+a1, c14+m15+a1, c14+m16+a1, c14+m17+a1, c14+m18+a1, c14+m19+a1, c14+m20+a1, c14+m21+a1, c14+m22+a1, c14+m23+a1, c14+m24+a1, c14+m25+a1, c14+m26+a1, c14+m27+a1, c14+m28+a1, c14+m29+a1, c14+m30+a1, c14+m31+a1, c14+m32+a1, c14+m33+a1, c14+m34+a1, c14+m35+a1, c14+m36+a1, c14+m37+a1, c14+m38+a1, c14+m39+a1, c14+m40+a1, c14+m41+a1, c14+m42+a1, c14+m43+a1, c14+m44+a1, c14+m45+a1, c14+m46+a1, c14+m47+a1, c14+m48+a1, c14+m49+a1, c14+m50+a1, c14+m51+a1, c14+m1+a2, c14+m2+a2, c14+m3+a2, c14+m4+a2, c14+m5+a2, c14+m6+a2, c14+m7+a2, c14+m8+a2, c14+m9+a2, c14+m10+a2, c14+m11+a2, c14+m12+a2, c14+m13+a2, c14+m14+a2, c14+m15+a2, c14+m16+a2, c14+m17+a2, c14+m18+a2, c14+m19+a2, c14+m20+a2, c14+m21+a2, c14+m22+a2, c14+m23+a2, c14+m24+a2, c14+m25+a2, c14+m26+a2, c14+m27+a2, c14+m28+a2, c14+m29+a2, c14+m30+a2, c14+m31+a2, c14+m32+a2, c14+m33+a2, c14+m34+a2, c14+m35+a2, c14+m36+a2, c14+m37+a2, c14+m38+a2, c14+m39+a2, c14+m40+a2, c14+m41+a2, c14+m42+a2, c14+m43+a2, c14+m44+a2, c14+m45+a2, c14+m46+a2, c14+m47+a2, c14+m48+a2, c14+m49+a2, c14+m50+a2, c14+m51+a2, c14+m1+a3, c14+m2+a3, c14+m3+a3, c14+m4+a3, c14+m5+a3, c14+m6+a3, c14+m7+a3, c14+m8+a3, c14+m9+a3, c14+m10+a3, c14+m11+a3, c14+m12+a3, c14+m13+a3, c14+m14+a3, c14+m15+a3, c14+m16+a3, c14+m17+a3, c14+m18+a3, c14+m19+a3, c14+m20+a3, c14+m21+a3, c14+m22+a3, c14+m23+a3, c14+m24+a3, c14+m25+a3, c14+m26+a3, c14+m27+a3, c14+m28+a3, c14+m29+a3, c14+m30+a3, c14+m31+a3, c14+m32+a3, c14+m33+a3, c14+m34+a3, c14+m35+a3, c14+m36+a3, c14+m37+a3, c14+m38+a3, c14+m39+a3, c14+m40+a3, c14+m41+a3, c14+m42+a3, c14+m43+a3, c14+m44+a3, c14+m45+a3, c14+m46+a3, c14+m47+a3, c14+m48+a3, c14+m49+a3, c14+m50+a3, c14+m51+a3, c14+m1+a4, c14+m2+a4, c14+m3+a4, c14+m4+a4, c14+m5+a4, c14+m6+a4, c14+m7+a4, c14+m8+a4, c14+m9+a4, c14+m10+a4, c14+m11+a4, c14+m12+a4, c14+m13+a4, c14+m14+a4, c14+m15+a4, c14+m16+a4, c14+m17+a4, c14+m18+a4, c14+m19+a4, c14+m20+a4, c14+m21+a4, c14+m22+a4, c14+m23+a4, c14+m24+a4, c14+m25+a4, c14+m26+a4, c14+m27+a4, c14+m28+a4, c14+m29+a4, c14+m30+a4, c14+m31+a4, c14+m32+a4, c14+m33+a4, c14+m34+a4, c14+m35+a4, c14+m36+a4, c14+m37+a4, c14+m38+a4, c14+m39+a4, c14+m40+a4, c14+m41+a4, c14+m42+a4, c14+m43+a4, c14+m44+a4, c14+m45+a4, c14+m46+a4, c14+m47+a4, c14+m48+a4, c14+m49+a4, c14+m50+a4, c14+m51+a4, c15+m1+a1, c15+m2+a1, c15+m3+a1, c15+m4+a1, c15+m5+a1, c15+m6+a1, c15+m7+a1, c15+m8+a1, c15+m9+a1, c15+m10+a1, c15+m11+a1, c15+m12+a1, c15+m13+a1, c15+m14+a1, c15+m15+a1, c15+m16+a1, c15+m17+a1, c15+m18+a1, c15+m19+a1, c15+m20+a1, c15+m21+a1, c15+m22+a1, c15+m23+a1, c15+m24+a1, c15+m25+a1, c15+m26+a1, c15+m27+a1, c15+m28+a1, c15+m29+a1, c15+m30+a1, c15+m31+a1, c15+m32+a1, c15+m33+a1, c15+m34+a1, c15+m35+a1, c15+m36+a1, c15+m37+a1, c15+m38+a1, c15+m39+a1, c15+m40+a1, c15+m41+a1, c15+m42+a1, c15+m43+a1, c15+m44+a1, c15+m45+a1, c15+m46+a1, c15+m47+a1, c15+m48+a1, c15+m49+a1, c15+m50+a1, c15+m51+a1, c15+m1+a2, c15+m2+a2, c15+m3+a2, c15+m4+a2, c15+m5+a2, c15+m6+a2, c15+m7+a2, c15+m8+a2, c15+m9+a2, c15+m10+a2, c15+m11+a2, c15+m12+a2, c15+m13+a2, c15+m14+a2, c15+m15+a2, c15+m16+a2, c15+m17+a2, c15+m18+a2, c15+m19+a2, c15+m20+a2, c15+m21+a2, c15+m22+a2, c15+m23+a2, c15+m24+a2, c15+m25+a2, c15+m26+a2, c15+m27+a2, c15+m28+a2, c15+m29+a2, c15+m30+a2, c15+m31+a2, c15+m32+a2, c15+m33+a2, c15+m34+a2, c15+m35+a2, c15+m36+a2, c15+m37+a2, c15+m38+a2, c15+m39+a2, c15+m40+a2, c15+m41+a2, c15+m42+a2, c15+m43+a2, c15+m44+a2, c15+m45+a2, c15+m46+a2, c15+m47+a2, c15+m48+a2, c15+m49+a2, c15+m50+a2, c15+m51+a2, c15+m1+a3, c15+m2+a3, c15+m3+a3, c15+m4+a3, c15+m5+a3, c15+m6+a3, c15+m7+a3, c15+m8+a3, c15+m9+a3, c15+m10+a3, c15+m11+a3, c15+m12+a3, c15+m13+a3, c15+m14+a3, c15+m15+a3, c15+m16+a3, c15+m17+a3, c15+m18+a3, c15+m19+a3, c15+m20+a3, c15+m21+a3, c15+m22+a3, c15+m23+a3, c15+m24+a3, c15+m25+a3, c15+m26+a3, c15+m27+a3, c15+m28+a3, c15+m29+a3, c15+m30+a3, c15+m31+a3, c15+m32+a3, c15+m33+a3, c15+m34+a3, c15+m35+a3, c15+m36+a3, c15+m37+a3, c15+m38+a3, c15+m39+a3, c15+m40+a3, c15+m41+a3, c15+m42+a3, c15+m43+a3, c15+m44+a3, c15+m45+a3, c15+m46+a3, c15+m47+a3, c15+m48+a3, c15+m49+a3, c15+m50+a3, c15+m51+a3, c15+m1+a4, c15+m2+a4, c15+m3+a4, c15+m4+a4, c15+m5+a4, c15+m6+a4, c15+m7+a4, c15+m8+a4, c15+m9+a4, c15+m10+a4, c15+m11+a4, c15+m12+a4, c15+m13+a4, c15+m14+a4, c15+m15+a4, c15+m16+a4, c15+m17+a4, c15+m18+a4, c15+m19+a4, c15+m20+a4, c15+m21+a4, c15+m22+a4, c15+m23+a4, c15+ m24+a4, c15+m25+a4, c15+m26+a4, c15+m27+a4, c15+m28+a4, c15+m29+a4, c15+m30+a4, c15+m31+a4, c15+m32+a4, c15+m33+a4, c15+m34+a4, c15+m35+a4, c15+m36+a4, c15+m37+a4, c15+m38+a4, c15+m39+a4, c15+m40+a4, c15+m41+a4, c15+m42+a4, c15+m43+a4, c15+m44+a4, c15+m45+a4, c15+m46+a4, c15+m47+a4, c15+m48+a4, c15+m49+a4, c15+m50+a4, c15+m51+a4, c16+m1+a1, c16+m2+a1, c16+m3+a1, c16+m4+a1, c16+m5+a1, c16+m6+a1, c16+m7+a1, c16+m8+a1, c16+m9+a1, c16+m10+a1, c16+m11+a1, c16+m12+a1, c16+m13+a1, c16+m14+a1, c16+m15+a1, c16+m16+a1, c16+m17+a1, c16+m18+a1, c16+m19+a1, c16+m20+a1, c16+m21+a1, c16+m22+a1, c16+m23+a1, c16+m24+a1, c16+m25+a1, c16+m26+a1, c16+m27+a1, c16+m28+a1, c16+m29+a1, c16+m30+a1, c16+m31+a1, c16+m32+a1, c16+m33+a1, c16+m34+a1, c16+m35+a1, c16+m36+a1, c16+m37+a1, c16+m38+a1, c16+m39+a1, c16+m40+a1, c16+m41+a1, c16+m42+a1, c16+m43+a1, c16+m44+a1, c16+m45+a1, c16+m46+a1, c16+m47+a1, c16+m48+a1, c16+m49+a1, c16+m50+a1, c16+m51+a1, c16+m1+a2, c16+m2+a2, c16+m3+a2, c16+m4+a2, c16+m5+a2, c16+m6+a2, c16+m7+a2, c16+m8+a2, c16+m9+a2, c16+m10+a2, c16+m11+a2, c16+m12+a2, c16+m13+a2, c16+m14+a2, c16+m15+a2, c16+m16+a2, c16+m17+a2, c16+m18+a2, c16+m19+a2, c16+m20+a2, c16+m21+a2, c16+m22+a2, c16+m23+a2, c16+m24+a2, c16+m25+a2, c16+m26+a2, c16+m27+a2, c16+m28+a2, c16+m29+a2, c16+m30+a2, c16+m31+a2, c16+m32+a2, c16+m33+a2, c16+m34+a2, c16+m35+a2, c16+m36+a2, c16+m37+a2, c16+m38+a2, c16+m39+a2, c16+m40+a2, c16+m41+a2, c16+m42+a2, c16+m43+a2, c16+m44+a2, c16+m45+a2, c16+m46+a2, c16+m47+a2, c16+m48+a2, c16+m49+a2, c16+m50+a2, c16+m51+a2, c16+m1+a3, c16+m2+a3, c16+m3+a3, c16+m4+a3, c16+m5+a3, c16+m6+a3, c16+m7+a3, c16+m8+a3, c16+m9+a3, c16+m10+a3, c16+m11+a3, c16+m12+a3, c16+m13+a3, c16+m14+a3, c16+m15+a3, c16+m16+a3, c16+m17+a3, c16+m18+a3, c16+m19+a3, c16+m20+a3, c16+m21+a3, c16+m22+a3, c16+m23+a3, c16+m24+a3, c16+m25+a3, c16+m26+a3, c16+m27+a3, c16+m28+a3, c16+m29+a3, c16+m30+a3, c16+m31+a3, c16+m32+a3, c16+m33+a3, c16+m34+a3, c16+m35+a3, c16+m36+a3, c16+m37+a3, c16+m38+a3, c16+m39+a3, c16+m40+a3, c16+m41+a3, c16+m42+a3, c16+m43+a3, c16+m44+a3, c16+m45+a3, c16+m46+a3, c16+m47+a3, c16+m48+a3, c16+m49+a3, c16+m50+a3, c16+m51+a3, c16+m1+a4, c16+m2+a4, c16+m3+a4, c16+m4+a4, c16+m5+a4, c16+m6+a4, c16+m7+a4, c16+m8+a4, c16+m9+a4, c16+m10+a4, c16+m11+a4, c16+m12+a4, c16+m13+a4, c16+m14+a4, c16+m15+a4, c16+m16+a4, c16+m17+a4, c16+m18+a4, c16+m19+a4, c16+m20+a4, c16+m21+a4, c16+m22+a4, c16+m23+a4, c16+m24+a4, c16+m25+a4, c16+m26+a4, c16+m27+a4, c16+m28+a4, c16+m29+a4, c16+m30+a4, c16+m31+a4, c16+m32+a4, c16+m33+a4, c16+m34+a4, c16+m35+a4, c16+m36+a4, c16+m37+a4, c16+m38+a4, c16+m39+a4, c16+m40+a4, c16+m41+a4, c16+m42+a4, c16+m43+a4, c16+m44+a4, c16+m45+a4, c16+m46+a4, c16+m47+a4, c16+m48+a4, c16+m49+a4, c16+m50+a4, c16+m51+a4, c17+m1+a1, c17+m2+a1, c17+m3+a1, c17+m4+a1, c17+m5+a1, c17+m6+a1, c17+m7+a1, c17+m8+a1, c17+m9+a1, c17+m10+a1, c17+m11+a1, c17+m12+a1, c17+m13+a1, c17+m14+a1, c17+m15+a1, c17+m16+a1, c17+m17+a1, c17+m18+a1, c17+m19+a1, c17+m20+a1, c17+m21+a1, c17+m22+a1, c17+m23+a1, c17+m24+a1, c17+m25+a1, c17+m26+a1, c17+m27+a1, c17+m28+a1, c17+m29+a1, c17+m30+a1, c17+m31+a1, c17+m32+a1, c17+m33+a1, c17+m34+a1, c17+m35+a1, c17+m36+a1, c17+m37+a1, c17+m38+a1, c17+m39+a1, c17+m40+a1, c17+m41+a1, c17+m42+a1, c17+m43+a1, c17+m44+a1, c17+m45+a1, c17+m46+a1, c17+m47+a1, c17+m48+a1, c17+m49+a1, c17+m50+a1, c17+m51+a1, c17+m1+a2, c17+m2+a2, c17+m3+a2, c17+m4+a2, c17+m5+a2, c17+m6+a2, c17+m7+a2, c17+m8+a2, c17+m9+a2, c17+m10+a2, c17+m11+a2, c17+m12+a2, c17+m13+a2, c17+m14+a2, c17+m15+a2, c17+m16+a2, c17+m17+a2, c17+m18+a2, c17+m19+a2, c17+m20+a2, c17+m21+a2, c17+m22+a2, c17+m23+a2, c17+m24+a2, c17+m25+a2, c17+m26+a2, c17+m27+a2, c17+m28+a2, c17+m29+a2, c17+m30+a2, c17+m31+a2, c17+m32+a2, c17+m33+a2, c17+m34+a2, c17+m35+a2, c17+m36+a2, c17+m37+a2, c17+m38+a2, c17+m39+a2, c17+m40+a2, c17+m41+a2, c17+m42+a2, c17+m43+a2, c17+m44+a2, c17+m45+a2, c17+m46+a2, c17+m47+a2, c17+m48+a2, c17+m49+a2, c17+m50+a2, c17+m51+a2, c17+m1+a3, c17+m2+a3, c17+m3+a3, c17+m4+a3, c17+m5+a3, c17+m6+a3, c17+m7+a3, c17+m8+a3, c17+m9+a3, c17+m10+a3, c17+m11+a3, c17+m12+a3, c17+m13+a3, c17+m14+a3, c17+m15+a3, c17+m16+a3, c17+m17+a3, c17+m18+a3, c17+m19+a3, c17+m20+a3, c17+m21+a3, c17+m22+a3, c17+m23+a3, c17+m24+a3, c17+m25+a3, c17+m26+a3, c17+m27+a3, c17+m28+a3, c17+m29+a3, c17+m30+a3, c17+m31+a3, c17+m32+a3, c17+m33+a3, c17+m34+a3, c17+m35+a3, c17+m36+a3, c17+m37+a3, c17+m38+a3, c17+m39+a3, c17+m40+a3, c17+m41+a3, c17+m42+a3, c17+m43+a3, c17+m44+a3, c17+m45+a3, c17+m46+a3, c17+m47+a3, c17+m48+a3, c17+m49+a3, c17+m50+a3, c17+m51+a3, c17+m1+a4, c17+m2+a4, c17+m3+a4, c17+m4+a4, c17+m5+a4, c17+m6+a4, c17+m7+a4, c17+m8+a4, c17+m9+a4, c17+m10+a4, c17+m11+a4, c17+m12+a4, c17+m13+a4, c17+m14+a4, c17+m15+a4, c17+m16+a4, c17+m17+a4, c17+m18+a4, c17+m19+a4, c17+m20+a4, c17+m21+a4, c17+m22+a4, c17+m23+a4, c17+m24+a4, c17+m25+a4, c17+m26+a4, c17+m27+a4, c17+m28+a4, c17+m29+a4, c17+m30+a4, c17+m31+a4, c17+m32+a4, c17+m33+a4, c17+m34+a4, c17+m35+a4, c17+m36+a4, c17+m37+a4, c17+m38+a4, c17+m39+a4, c17+m40+a4, c17+m41+a4, c17+m42+a4, c17+m43+a4, c17+m44+a4, c17+m45+a4, c17+m46+a4, c17+m47+a4, c17+m48+a4, c17+m49+a4, c17+m50+a4, c17+m51+a4, c18+m1+a1, c18+m2+a1, c18+m3+a1, c18+m4+a1, c18+m5+a1, c18+m6+a1, c18+m7+a1, c18+m8+a1, c18+m9+a1, c18+m10+a1, c18+m11+a1, c18+m12+a1, c18+m13+a1, c18+m14+a1, c18+m15+a1, c18+m16+a1, c18+m17+a1, c18+m18+a1, c18+m19+a1, c18+m20+a1, c18+m21+a1, c18+m22+a1, c18+m23+a1, c18+m24+a1, c18+m25+a1, c18+m26+a1, c18+m27+a1, c18+m28+a1, c18+m29+a1, c18+m30+a1, c18+m31+a1, c18+m32+a1, c18+m33+a1, c18+m34+a1, c18+m35+a1, c18+m36+a1, c18+m37+a1, c18+m38+a1, c18+m39+a1, c18+m40+a1, c18+m41+a1, c18+m42+a1, c18+m43+a1, c18+m44+a1, c18+m45+a1, c18+m46+a1, c18+m47+a1, c18+m48+a1, c18+m49+a1, c18+m50+a1, c18+m51+a1, c18+m1+a2, c18+m2+a2, c18+m3+a2, c18+m4+a2, c18+m5+a2, c18+m6+a2, c18+m7+a2, c18+m8+a2, c18+m9+a2, c18+m10+a2, c18+m11+a2, c18+m12+a2, c18+m13+a2, c18+m14+a2, c18+m15+a2, c18+m16+a2, c18+m17+a2, c18+m18+a2, c18+m19+a2, c18+m20+a2, c18+m21+a2, c18+m22+a2, c18+m23+a2, c18+m24+a2, c18+m25+a2, c18+m26+a2, c18+m27+a2, c18+m28+a2, c18+m29+a2, c18+m30+a2, c18+m31+a2, c18+m32+a2, c18+m33+a2, c18+m34+a2, c18+m35+a2, c18+m36+a2, c18+m37+a2, c18+m38+a2, c18+m39+a2, c18+m40+a2, c18+m41+a2, c18+m42+a2, c18+m43+a2, c18+m44+a2, c18+m45+a2, c18+m46+a2, c18+m47+a2, c18+m48+a2, c18+m49+a2, c18+m50+a2, c18+m51+a2, c18+m1+a3, c18+m2+a3, c18+m3+a3, c18+m4+a3, c18+m5+a3, c18+m6+a3, c18+m7+a3, c18+m8+a3, c18+m9+a3, c18+ m10+a3, c18+m11+a3, c18+m12+a3, c18+m13+a3, c18+m14+a3, c18+m15+a3, c18+m16+a3, c18+m17+a3, c18+m18+a3, c18+m19+a3, c18+m20+a3, c18+m21+a3, c18+m22+a3, c18+m23+a3, c18+m24+a3, c18+m25+a3, c18+m26+a3, c18+m27+a3, c18+m28+a3, c18+m29+a3, c18+m30+a3, c18+m31+a3, c18+m32+a3, c18+m33+a3, c18+m34+a3, c18+m35+a3, c18+m36+a3, c18+m37+a3, c18+m38+a3, c18+m39+a3, c18+m40+a3, c18+m41+a3, c18+m42+a3, c18+m43+a3, c18+m44+a3, c18+m45+a3, c18+m46+a3, c18+m47+a3, c18+m48+a3, c18+m49+a3, c18+m50+a3, c18+m51+a3, c18+m1+a4, c18+m2+a4, c18+m3+a4, c18+m4+a4, c18+m5+a4, c18+m6+a4, c18+m7+a4, c18+m8+a4, c18+m9+a4, c18+m10+a4, c18+m11+a4, c18+m12+a4, c18+m13+a4, c18+m14+a4, c18+m15+a4, c18+m16+a4, c18+m17+a4, c18+m18+a4, c18+m19+a4, c18+m20+a4, c18+m21+a4, c18+m22+a4, c18+m23+a4, c18+m24+a4, c18+m25+a4, c18+m26+a4, c18+m27+a4, c18+m28+a4, c18+m29+a4, c18+m30+a4, c18+m31+a4, c18+m32+a4, c18+m33+a4, c18+m34+a4, c18+m35+a4, c18+m36+a4, c18+m37+a4, c18+m38+a4, c18+m39+a4, c18+m40+a4, c18+m41+a4, c18+m42+a4, c18+m43+a4, c18+m44+a4, c18+m45+a4, c18+m46+a4, c18+m47+a4, c18+m48+a4, c18+m49+a4, c18+m50+a4, c18+m51+a4, c19+m1+a1, c19+m2+a1, c19+m3+a1, c19+m4+a1, c19+m5+a1, c19+m6+a1, c19+m7+a1, c19+m8+a1, c19+m9+a1, c19+m10+a1, c19+m11+a1, c19+m12+a1, c19+m13+a1, c19+m14+a1, c19+m15+a1, c19+m16+a1, c19+m17+a1, c19+m18+a1, c19+m19+a1, c19+m20+a1, c19+m21+a1, c19+m22+a1, c19+m23+a1, c19+m24+a1, c19+m25+a1, c19+m26+a1, c19+m27+a1, c19+m28+a1, c19+m29+a1, c19+m30+a1, c19+m31+a1, c19+m32+a1, c19+m33+a1, c19+m34+a1, c19+m35+a1, c19+m36+a1, c19+m37+a1, c19+m38+a1, c19+m39+a1, c19+m40+a1, c19+m41+a1, c19+m42+a1, c19+m43+a1, c19+m44+a1, c19+m45+a1, c19+m46+a1, c19+m47+a1, c19+m48+a1, c19+m49+a1, c19+m50+a1, c19+m51+a1, c19+m1+a2, c19+m2+a2, c19+m3+a2, c19+m4+a2, c19+m5+a2, c19+m6+a2, c19+m7+a2, c19+m8+a2, c19+m9+a2, c19+m10+a2, c19+m11+a2, c19+m12+a2, c19+m13+a2, c19+m14+a2, c19+m15+a2, c19+m16+a2, c19+m17+a2, c19+m18+a2, c19+m19+a2, c19+m20+a2, c19+m21+a2, c19+m22+a2, c19+m23+a2, c19+m24+a2, c19+m25+a2, c19+m26+a2, c19+m27+a2, c19+m28+a2, c19+m29+a2, c19+m30+a2, c19+m31+a2, c19+m32+a2, c19+m33+a2, c19+m34+a2, c19+m35+a2, c19+m36+a2, c19+m37+a2, c19+m38+a2, c19+m39+a2, c19+m40+a2, c19+m41+a2, c19+m42+a2, c19+m43+a2, c19+m44+a2, c19+m45+a2, c19+m46+a2, c19+m47+a2, c19+m48+a2, c19+m49+a2, c19+m50+a2, c19+m51+a2, c19+m1+a3, c19+m2+a3, c19+m3+a3, c19+m4+a3, c19+m5+a3, c19+m6+a3, c19+m7+a3, c19+m8+a3, c19+m9+a3, c19+m10+a3, c19+m11+a3, c19+m12+a3, c19+m13+a3, c19+m14+a3, c19+m15+a3, c19+m16+a3, c19+m17+a3, c19+m18+a3, c19+m19+a3, c19+m20+a3, c19+m21+a3, c19+m22+a3, c19+m23+a3, c19+m24+a3, c19+m25+a3, c19+m26+a3, c19+m27+a3, c19+m28+a3, c19+m29+a3, c19+m30+a3, c19+m31+a3, c19+m32+a3, c19+m33+a3, c19+m34+a3, c19+m35+a3, c19+m36+a3, c19+m37+a3, c19+m38+a3, c19+m39+a3, c19+m40+a3, c19+m41+a3, c19+m42+a3, c19+m43+a3, c19+m44+a3, c19+m45+a3, c19+m46+a3, c19+m47+a3, c19+m48+a3, c19+m49+a3, c19+m50+a3, c19+m51+a3, c19+m1+a4, c19+m2+a4, c19+m3+a4, c19+m4+a4, c19+m5+a4, c19+m6+a4, c19+m7+a4, c19+m8+a4, c19+m9+a4, c19+m10+a4, c19+m11+a4, c19+m12+a4, c19+m13+a4, c19+m14+a4, c19+m15+a4, c19+m16+a4, c19+m17+a4, c19+m18+a4, c19+m19+a4, c19+m20+a4, c19+m21+a4, c19+m22+a4, c19+m23+a4, c19+m24+a4, c19+m25+a4, c19+m26+a4, c19+m27+a4, c19+m28+a4, c19+m29+a4, c19+m30+a4, c19+m31+a4, c19+m32+a4, c19+m33+a4, c19+m34+a4, c19+m35+a4, c19+m36+a4, c19+m37+a4, c19+m38+a4, c19+m39+a4, c19+m40+a4, c19+m41+a4, c19+m42+a4, c19+m43+a4, c19+m44+a4, c19+m45+a4, c19+m46+a4, c19+m47+a4, c19+m48+a4, c19+m49+a4, c19+m50+a4, c19+m51+a4.

Pressure

The catalytic hydrogenation according to the invention is preferably performed under elevated pressure (i.e. up to about 600 bar), preferably in an autoclave in a hydrogen gas atmosphere, preferably in a semi batch hydrogenation process. The (additional) pressure increase can be brought about by supply of an inert gas, such as nitrogen or argon. The hydrogenation according to the invention is effected preferably at a hydrogen pressure in the range from about 0 to about 300 bar, more preferably at a hydrogen pressure in the range from about 5 to about 200 bar. Preferred ranges of hydrogen pressure are also e from about 0.5 to about 150 bar.

In one embodiment the catalytic hydrogenation according to the invention is preferably performed under elevated pressure (i.e. up to about 200 bar).

The hydrogen pressure according to the invention can also vary during the process.

If necessary, suitable measures for dissipating heat from the exothermic reaction can be applied.

Temperature

The catalytic hydrogenation according to the invention is performed preferably at a temperature in the range from about −20° C. to about 200° C., more preferably at a temperature in the range from about 0° C. to about 100° C., most preferably in the range from about 5 to 70° C.

Solvents

The catalytic hydrogenation can also be performed without a solvent. However, it is generally advantageous to perform the process according to the invention in the presence of solvents (diluents). Solvents are advantageously used in such an amount that the reaction mixture remains efficiently stirrable over the entire process. Advantageously, based on the nitrile used, 1 to 50 times the amount of solvent, preferably 2 to 40 times the amount of solvent and more preferably 2 to 30 times the amount of solvent is used.

Useful solvents for the performance of the hydrogenation process according to the invention include water and all organic solvents which are inert under the reaction conditions, the type of solvent used depending on the type of reaction procedure, more particularly on the type of catalyst used and/or the hydrogen source (introduction of gaseous hydrogen or generation in situ). Solvents are also understood in accordance with the invention to mean mixtures of pure solvents.

Solvents suitable in accordance to the invention are water, acids such as acetic acid, acetic anhydride, alcohols such as methanol, ethanol, isopropanol, butanol, t-amyl alcohol, benzyl alcohol, 1,3-butanediol, 1,4-butanediol, 2-butoxyethanol, cyclohexanol, diethylene glycol, diethylene glycol methyl ether, dipropylene glycol, dipropylene glycol methyl ether, 2-ethoxyethanol, ethanolamine, ethylene glycol, glycerol, hexanole, hexylene glycol, isoamyl alcohol, isobutanol, 2-methoxyethanol, 1-octanol, pentanol, propylene glycol, tetraethylene glycol, triethylene glycol; ethers, such as ethyl propyl ether, methyl tert-butyl ether, n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyl tetrahydrofuran, methyl cyclopenthylether, dioxane, dichlorodiethyl ether, petroleum ether, ligroin and polyethers of ethylene oxide and/or propylene oxide; ketones such as acetone, cyclohexanone, 3-pentanone, amines, such as trimethyl-, triethyl-, tripropyl-, and tributylamine, tert-amyl methyl ether (TAME), N-methyl morpholine, aliphatic, cycloaliphatic or aromatic hydrocarbons such as pentane, hexane, methyl cyclohexane heptane, octane, nonane, and technical-grade hydrocarbons which may be substituted by fluorine and chlorine atoms, such as dichloromethane, fluorobenzene, chlorobenzene or dichlorobenzene, for example white spirits having components with boiling points in the range, for example, from 40° C. to 250° C., cymene, petroleum fractions within a boiling range from 70° C. to 190° C., toluene, xylenes, ethylbenzene. esters such as amyl acetates, butyl acetates, ethyl acetate, isobutyl acetate, isopropyl acetate, 2-methoxyethyl acetate, methyl acetate, propyl acetate, prop glycol methyl ether acetate, carbonate such as propylene carbonate, dimethyl carbonate, diethyl carbonate; N,N-Dimethylacetimide, N,N-Dimethylformamide, 2-pyrrolidone and N-methyl pyrrolidone.

In the process according to the invention, it is preferred to use alcohols or cyclic ethers as solvent. Preferred is methanol, ethanol, isopropanol, t-butanol, tetrahydrofuran, or methyltetrahydrofuran. Among before mentioned solvents methanol is preferred. It is further preferred that from the group of suitable solvents to be used in the hydrogenation reaction acids such as acetic acid and acetic anhydride are excluded.

The solvents, which may be used in the additional process steps following the hydrogenation step (A1) may be independently selected from the solvents as defined above for the hydrogenation step (A1).

The solvents which can be used in step (A1), (A3) and (A5) can be the same or different and can independently in each case be used as mixtures of solvents, in particular mixtures comprising water or as solvents consisting of only one component.

Route B

Another aspect the present invention describes a process (B) for the production of a compound according to formula (I)

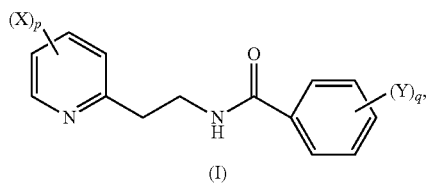

wherein p and X are defined as above;
q is an integer equal to 1, 2, 3 or 4;
each substituent Y is chosen, independently of the others, as being halogen, $C_1$-$C_4$ alkyl or $C_1$-$C_4$ haloalkyl;
wherein in the first step (B1)
a substituted 2-methyl cyanopyridyl derivative according to formula (II)

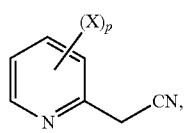

wherein p and X are defined as above;

is hydrogenated in the presence of a metal catalyst, an catalyst modifier, and an acid to
a substituted 2-ethylaminopyridine derivative according to the formula (III) or corresponding salts thereof,

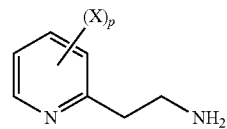

wherein X, p are defined as above;
where in the second step (B2) a substituted 2-ethylaminopyridine derivative according to the formula (III) as defined in step (B1) is reacted with a benzoyl halide according to formula (IV)

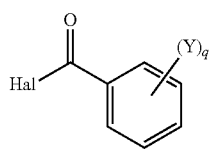

wherein
Hal is fluorine, chlorine or bromine;
q is an integer equal to 1, 2, 3 or 4;
each substituent Y is chosen, independently of the others, as being halogen, $C_1$-$C_4$ alkyl or $C_1$-$C_4$ haloalkyl;
to the compound according to formula (I).

Preferably the compound according to formula (I) is Fluopyram (N-[2-[3-chloro-5-(trifluoromethyl)-2-pyridinyl]ethyl]-2-(trifluoromethyl)benzamide, the compound according to formula (Ia).

Optionally in the third step (B3) a solvent and an acid are added to the reaction mixture comprising the precipitated compound according to formula (I).

Optionally in the third step (B3) the aqueous phase can be removed from the reaction mixture.

Optionally in the fourth step (B4) the organic phase comprising the compound according to formula (I) is separated from the phase comprising water.

q is preferably 1 or 2.
q is very preferably 1.

In each case, Y is preferably independently of the others, as being fluorine, chlorine, bromine, $C_1$-$C_2$ alkyl or $C_1$-$C_2$ haloalkyl having 1 to 5 halogen atoms selected independently from each other from fluorine, chlorine;

In each case, Y is more preferably independently of the others, as being fluorine, chlorine, methyl, ethyl or $C_1$-$C_2$ haloalkyl having 1 to 5 halogen atoms selected independently from each other from fluorine, chlorine;

In each case, Y is particular preferably independently of the others, as being fluorine, chlorine, or difluoromethyl, trifluoromethyl, dichloromethyl, trichloromethyl;

In each case, Y is very particular preferably trifluoromethyl.

In each case, Y is very particular preferably chlorine.

As regards the positions in which the phenyl moiety is substituted by Y, the phenyl moiety is preferably substituted by Y in 2- and/or in 6-position. Preferably, the phenyl moiety is substituted by Y in 2-position.

Very particular preferably the compound according to formula (II) is 3-chloro-5-(trifluoromethyl)pyridin-2-yl]acetonitrile and the compound according to formula (III) is 2-[3-chloro-5-(trifluoromethyl)pyridin-2-yl]ethanamine. Very preferably the compound according to formula (IV) is 2-trifluoromethyl-benzoyl chloride.

Very preferably the compound according to formula (I) is fluopyram as defined in formula (Ia).

The corresponding salts of the compounds according to formula (III) are preferably hydrogensulfates, sulfates, hydrochlorides, phosphates, formiates, or acetates.

Regarding the metal catalyst, the catalyst modifier and the acid used in step (B1), reference is made to the definitions and amounts as provided above for step (A1).

Preferably step (B2) is performed in the presence of a base.

Useful bases used in step (B2) are inorganic and/or organic bases such as $Na_2CO_3$, $NaHCO_3$, $K_2CO_3$, $KHCO_3$, NaOH, KOH, $Ca(OH)_2$, $Mg(OH)_2$, triethyl amine, N,N-diisopropylethylamine.

The following bases are particularly preferred for step (B2): $Na_2CO_3$, $NaHCO_3$, $K_2CO_3$, $KHCO_3$, NaOH, KOH, $Ca(OH)_2$. More preferred are NaOH, KOH, $Ca(OH)_2$. Mostly preferred are NaOH, KOH. Preferably, in step (B2) a base as defined herein is added until adjustment of the pH value of the reaction solution to pH 4 to 14, preferably pH 6 bis 13 is achieved.

The following bases are particularly preferred for step (B2): $Na_2CO_3$, $NaHCO_3$, $K_2CO_3$, $KHCO_3$, NaOH, KOH, $Ca(OH)_2$. More preferred are NaOH, KOH, $Ca(OH)_2$. Mostly preferred are NaOH, KOH. Preferably, in step (B2) a base as defined herein is added until adjustment of the pH value of the reaction solution to pH 4 to 14, preferably pH 6 bis 13 is achieved.

The acid, which may be used in the additional steps following the hydrogenation reaction of step (B1), particularly in step (B3), as well as the amount of acid used therein is defined as above for process step (A4).

The solvent as well as the amount of solvent used in steps (B1), (B2), and (B3) is defined as above for process (A).

The hydrogen pressure used in step (B1) is defined as above for process (A).

Temperature

The process step (B1) according to the invention is performed preferably at a temperature in the range from about −20° C. to about 250° C., more preferably at a temperature in the range from about 0° C. to about 175° C., most preferably in the range from about 0 to 150° C.

The process (B2) according to the invention is performed preferably at a temperature in the range from about −20° C. to about 250° C., more preferably at a temperature in the range from about 0° C. to about 175° C., most preferably in the range from about 0 to 150° C.

The process (B3) according to the invention is performed preferably at a temperature in the range from about −20° C. to about 250° C., more preferably at a temperature in the range from about 0° C. to about 175° C., most preferably in the range from about 0 to 150° C.

The process (B4) according to the invention is performed preferably at a temperature in the range from about −20° C. to about 250° C., more preferably at a temperature in the range from about 0° C. to about 175° C., most preferably in the range from about 0 to 150° C.

EXAMPLES

The examples shown below further illustrate the invention without limiting it.

Examples Regarding Process (A)

Example 1: Hydrogenation with Different Catalyst, Different Modifiers and Sulfuric Acid An autoclave is charged with a solution of [3-chloro-5-(trifluoromethyl)pyridin-2-yl]acetonitrile [Py-CN], a modifier at a concentration between 0.0001 to 0.1 equivalents related to the amount of [PyCN] and an acid in a solvent, followed by the addition of the catalyst. The catalyst, modifier, acid, and solvent can be chosen from the tables 1a, 1b, 1c and 1d below.

The contents are then stirred at an elevated hydrogen pressure of more than 5 bar at 20° C. for 4 h—hydrogen uptake ceased after 3 hours and stirring is continued for another hour. The reaction mixture is removed by filtration from the autoclave. In case of recyclization the above described procedure is repeated under the same conditions as described above. The removed reaction mixture is analyzed by HPLC to quantify the content of amine.

TABLE 1a

| Catalysts |
| The catalysts are commercially available catalysts |
| from companies (e.g. BASF, Acros, Evonik). |

| Ref. | Catalyst |
| --- | --- |
| c1 | Pd |
| c2 | Pd/C |
| c3 | $Pd(OH)_2$/C |
| c4 | Pd/$Al_2O_3$ |
| c5 | Palladium oxide/C |
| c6 | mixed Palladium oxide-hydroxide/C |
| c7 | Palladium oxide/$Al_2O_3$ |
| c8 | mixed Palladium oxide-hydroxide/$Al_2O_3$ |
| c9 | Palladium/$SiO_2$ |
| c10 | Palladium oxide/$SiO_2$ |
| c11 | mixed Palladium oxide-hydroxide/$SiO_2$ |
| c12 | Pd/$CaCO_3$ |
| c13 | Pd/C-diphenylsulfide |
| c14 | Pd/$BaSO_4$ |
| c15 | Pd(II)acetate-Polymethylhydrosiloxane |
| c16 | Pd (Fe)/C |
| c17 | Pd/C 5% sulfur |
| c18 | 5% Pd/0.5% V |
| c19 | Pd/Pt |

TABLE 1b

| Modifier | |
| --- | --- |
| Ref. | Modifier |
| m1 | Thiophene |
| m2 | Tetrahydrothiophene |
| m3 | 2-Mercaptophenol |
| m4 | Cysteine |
| m5 | 3,6-Dithia 1,8 octadiol |
| m6 | 2,2'-Thiobisethanol |
| m7 | Diphenyl sulfide |
| m8 | Thiophenol |
| m9 | Thioanisole |
| m10 | Sulfolane |
| m11 | Thiourea |
| m12 | $Na_2S_2O_3$—$xH_2O$ |
| m13 | $Na_2S$ |

TABLE 1b-continued

Modifier

| Ref. | Modifier |
|---|---|
| m14 | Chinoline |
| m15 | PPh$_3$ |
| m16 | Mo(CO)$_6$ |
| m17 | V(V) oxide |
| m18 | V(IV) oxide |
| m19 | V(III) sulfide |
| m20 | NH$_4$VO$_3$ |
| m21 | ZnBr$_2$ |
| m22 | ZnCl$_2$ |
| m23 | MgBr$_2$ |
| m24 | MgO |
| m25 | FeCl$_2$ |
| m26 | FeCl$_3$ |
| m27 | Fe(OAc)$_2$) |
| m28 | n-Tetramethylammonium iodide |
| m29 | n-Tetraethylammonium iodide |
| m30 | n-Tetrabutylammonium iodide |
| m31 | n-Tetramethylammonium bromide (TMAB) |
| m32 | n-Tetraethylammonium bromide |
| m33 | n-Tetrabutylammoniumbromide (TBAB) |
| m34 | n-Tetramethylammonium chloride |
| m35 | n-Tetraethylammonium chloride |
| m36 | n-Tetrabutylammoniumchloride |
| m37 | NaCl |
| m38 | NaBr |
| m39 | NaI |
| m40 | KCl |
| m41 | KBr |
| m42 | KI |
| m43 | LiBr |
| m44 | MgBr$_2$ |
| m45 | AlCl$_3$ |
| m46 | CeCl$_3$ |
| m47 | CuCl |
| m48 | CuBr |
| m49 | CuI |
| m50 | CuBr$_2$ |
| m51 | BaSO$_4$ |

TABLE 1c

Acid

| Ref. | Acid |
|---|---|
| a1 | Sulfuric acid |
| a2 | HCl |
| a3 | Phosphoric acid |
| a4 | Methanesulfonic acid |

TABLE 1d

Solvent

| Ref. | Solvent |
|---|---|
| s1 | Methanol |
| s2 | Ethanol |
| s3 | isopropanol |
| s4 | t-butanol |
| s5 | tetrahydrofuran |
| s6 | methyltetrahydrofuran |

From the tables 1a, 1b, 1c and 1d any combination of catalyst, modifier, acid and solvent c1m1a1s1 to c19m51a4s6 can be selected.

Example 2: Hydrogenation with Different Catalysts, Different Modifiers and Sulfuric Acid An autoclave was charged with a solution of [3-chloro-5-(trifluoromethyl)pyridin-2-yl]acetonitrile [Py-CN], modifier as listed in table 2a and 2b below at a concentration between 0.0001 to 0.1 equivalents related to the amount of [PyCN] and sulfuric acid in methanol, followed by the addition of the catalyst as listed in table 2a and 2b below. The catalysts are commercially available catalysts from companies (e.g. BASF, Acros, Evonik). The contents were then stirred at an elevated hydrogen pressure of more than 5 bar at 20° C. for 4 h—hydrogen uptake ceased after 3 hours and stirring was continued for another hour. The reaction mixture was removed by filtration from the autoclave. In case of recyclization the above described procedure was repeated under the same conditions as described above. The removed reaction mixture was analyzed by HPLC to quantify the content of amine. The HPLC yield of 2-[3-chloro-5-(trifluoromethyl)pyridin-2-yl]ethanamine is shown in table 2a and 2b below.

TABLE 2a

| Entry | Catalyst [mol %] | Modifier [mol %] | yield [%] | Deschloro HPLC [area-%] |
|---|---|---|---|---|
| 1 | 5% Pd/C | KBr | 83.7 | |
| 2 | 5% Pd/C | Fe(OAc)$_2$ | 50.6 | 38.22 |
| 3 | 5% Pd/C | BaSO$_4$ | 52.1 | 38.45 |
| 4 | 5% Pd + 0.5% V 2 mol % | NaBr 3.3 mol % | 75.3 | 3.45 |
| 5 | 4% Pd 1% Pt 2 mol % | TBAB 3.3 mol % | 51.1 | 10.10 |
| 6a | 10% Pd/C | NaBr | 86.7 | 7.33 |
| 6b | 10% Pd/C | TBAB | 84.4 | 10.50 |
| 7 | 10% Pd/C | KBr | 78.6 | |
| 8a | 10% Pd/C 2 mol % | Na$_2$S$_2$O$_3$—xH$_2$O 0.5 mol % | 49.7 | 5.56 |
| 8b | 10% Pd/C 3 mol % | TBAB 5 mol % | 85.8 | 10.7 |
| 9 | 10% Pd/C 2 mol % | PPh$_3$ 3 mol % | 0.4 | 0 |
| 10 | 20% Pd(OH)$_2$/C 2 mol % | Ba$_2$SO$_4$ | 59.6 | 33.68 |
| 11 | 20% Pd (Cat No 1) 2 mol % | NaBr 3 mol % | 88.3 | 4.15 |
| 12 | 20% Pd (Cat No 1) 2 mol % | TBAB 3 mol % | 89.2 | 4.43 |
| 13 | 20% Pd (Cat No 1) 2 mol % | ZnBr$_2$ 3 mol % | 76.7 | 4.57 |
| 14 | 20% Pd (Cat No 1) 2 mol % | Cysteine 0.5 mol % | 49.7 | 7.86 |
| 15 | 20% Pd (Cat No 2) 3 mol % | TBAB 5 mol % | 90.9 | 4.89 |
| 16 | 20% Pd (Cat No 3) 3 mol % | TBAB 5 mol % | 91.1 | 4.96 |
| 17 | 20% Pd (Cat No 4) 3 mol % | TBAB 5 mol % | 91.0 | 5.40 |
| 18 | 20% Pd (Cat No 5) 3 mol % | TBAB 5 mol % | 90.3 | 5.16 |
| 19 | 20% Pd (Cat No 6) 3 mol % | TBAB 5 mol % | 90.1 | 5.27 |
| 20 | Rh/C | TBAB 3.3 mol % | 16.25 | 0 |
| 21 | Pt/C | TBAB 3.3 mol % | 4.30 | 0.21 |

Comparative Example

TABLE 2b

| Entry | Catalyst [mol %] | Modifier [mol %] | yield [%] | Deschloro HPLC [area-%] |
|---|---|---|---|---|
| 22 | 5% Pd + 0.5% V 2 mol % | without modifier | 62.9 | 19.17 |

Example 3: Hydrogenation with Palladium Catalyst, Different Modifiers and Sulfuric Acid An autoclave was charged with a solution of [3-chloro-5-(trifluoromethyl)pyridin-2-yl]acetonitrile [Py-CN], a modifier as listed below in table 3 and sulfuric acid in methanol, followed by the addition of $Pd(OH)_2$/on carbon. The contents were then stirred at an elevated hydrogen pressure of more than 5 bar at 20° C. for 1-4 h—hydrogen uptake ceased after 1-3 hours and stirring was continued for another hour. The reaction mixture was removed by filtration from the autoclave. The removed reaction mixture was analyzed by HPLC to quantify the content of amine. After filtration of the catalyst the methanolic solution is evaporated in vacuo. The residue was re-dissolved in water and evaporated again to remove remaining methanol. The mixture is cooled down to 10° C. followed by addition of a base to adjust the pH to 7-14. Then solvent (e. g. toluene, xylene, methylcyclohexane, tetrahydrofurane, methyltertbutylether) can be added to the solution and the organic phase is separated. The water phase is extracted again with a suitable solvent. To this mixture an acid (e.g. hydrochloric acid (gaseous or aqueous) can be added slowly, optionally followed by a distillation step. The amine salt e.g. amine hydrochloride precipitated out. Then a defined amount of water and organic solvent, if necessary, can be added to the solution. The solid was filtrated, washed with e.g. toluene and dried under reduced pressure.

The results are shown in table 3a and 3b below for the different modifiers.

TABLE 3a

| Entry | Modifier | yield [%] | Deschloro HPLC [area-%] |
|---|---|---|---|
| 1 | V(V)oxid 5 mol % | 56.5 | 31.79 |
| 2 | V(IV)oxid 5 mol % | 60.3 | 30.33 |
| 3 | V(III)sulfide (0.1 mol %) | 54.9 | 37.5 |
| 4 | V(III)sulfide (5 mol %) | 0.9 | 0.09 |
| 5 | MgO 5 mol % | 42.6 | 7.21 |
| 6 | $ZnBr_2$ 5 mol % | 76.1 | 1.67 |
| 7 | $NH_4VO_3$ 5 mol % | 64.6 | 24.7 |
| 8 | 1 mol % CuI | 7.8 | 0.05 |
| 8 | 5 mol % $FeCl_3$ | 70.6 | 13.36 |
| 9 | 5 mol % Fe(OAc)$_2$ | 61.7 | 27.25 |
| 10 | 1 mol % NaI | 1.4 | 0 |
| 11 | 1 mol % KI | 0.3 | 0 |
| 12 | TMAB | 86.1 | 6.08 |
| 13 | TBAB | 91 | 5 |
| 14 | 4 mol % Thiourea | 0.1 | 0 |
| 15 | 1800 ppm 3,6-dithia-1,8-octadiole | 60.3 | 8.1 |
| 16 | Tetrahydrothiophene | >70 | |
| 17 | $PPh_3$ 0.20 mol % | 81 | 8.08 |
| 18 | NaBr | 91.34 | 4.06 |
| 19 | KBr 2 mol % | 86.8 | 8.61 |
| 20 | 2-Mercaptophenol | 49.8 | |
| 21 | 2-Mercaptophenol 1.57 mg | 41.5 | |
| 21 | Chinolin 5 mol % | 57.4 | 10.14 |
| 22 | Mo(CO)6 0.002 mol % | 33.5 | 4.86 |

Comparative Example

To show the effect of the specific combination of the present invention, a hydrogenation reaction was carried out as described in Example 3, wherein the [3-chloro-5-(trifluoromethyl)pyridin-2-yl]acetonitrile [Py-CN] was hydrogenated
  a) without adding an acid and without adding a modifier (Table 3b, Entry 1),
  b) in the presence of an acid without adding a modifier (Table 3b, Entry 2),
  c) in the presence of a catalyst modifier without adding an acid (Table 3b, Entry 3), and
  d) in the presence of a modifier and an acid, according to the present invention, (Table 3b, Entry 4).

The results are shown in table 3b:

TABLE 3b

| Entry | Catalyst [mol %] | Modifier [mol %] | Acid [mol %] | yield [%] | Deschloro HPLC [area-%] |
|---|---|---|---|---|---|
| 1 | $Pd(OH)_2$/C 2 | — | — | 14.78 | 8.20 |
| 2 | $Pd(OH)_2$/C 2 | — | $H_2SO_4$ 120 | 62.9 | 28.6 |
| 3 | $Pd(OH)_2$/C 2 | TBAB 3.3 | — | 13.26 | 3.84 |
| 4 | $Pd(OH)_2$/C 2 | TBAB 3.3 | $H_2SO_4$ 120 | 91.0 | 5.0 |

The Comparative Example clearly shows that only the specific combination of the present invention, comprising a palladium catalyst, a catalyst modifier and an acid, achieves improved yields and reduced contents of the dechlorinated side product 2-[5-(trifluoromethyl)pyridin-2-yl]ethanamine.

Example 4: Hydrogenation with the Catalyst Pd(OH)2/C, Different Solvents and Sulfuric Acid An autoclave was charged with a solution of [3-chloro-5-(trifluoromethyl)pyridin-2-yl]acetonitrile [Py-CN], TBAB or TMAB at a concentration between 1 to 5 w/w % related to the amount of [Py-CN] and the solvent as listed below, followed by the addition of $Pd(OH)_2$ on carbon. The contents were then stirred at an elevated hydrogen pressure of more than 5 bar at 20° C. for 4 h—hydrogen uptake ceased after 3 hours and stirring was continued for another hour. The reaction mixture was removed by filtration from the autoclave. The removed reaction mixture was analyzed by HPLC to quantify the content of amine. The HPLC yield of 2-[3-chloro-5-(trifluoromethyl)pyridin-2-yl]ethanamine is shown in table 4 below.

TABLE 4

| Solvent | HPLC-yield [%] |
|---|---|
| AcOH/water | >70% |
| Ethanol | >60% |
| Methanol | >70% |
| Tetrahydrofuran | >40% |

Example 5: Hydrogenation with the Catalyst $Pd(OH)_2$/C or Pd/C, in MeOH and Different Acids An autoclave was charged with a solution of [3-chloro-5-(trifluoromethyl)pyridin-2-yl]acetonitrile [Py-CN], TBAB or TMAB at a concentration between 1 to 5 w/w % related to the amount of [Py-CN] and an acid as listed below in methanol, followed by the addition of Pd(OH)₂ on carbon or Pd/C. The contents were then stirred at an elevated hydrogen pressure of more than 5 bar at 20° C. for 4 h—hydrogen uptake ceased after 3 hours and stirring was continued for another hour. The reaction mixture was removed by filtration from the autoclave. In case of recyclization the above described procedure was repeated under the same conditions as described above. The removed reaction mixture was analyzed by HPLC to quantify the content of amine. The HPLC yield of 2-[3-chloro-5-(trifluoromethyl)pyridin-2-yl] ethanamine is shown in table 5 below.

TABLE 5

| Acid | HPLC-yield [%] |
|---|---|
| HCl | >70% |
| Acetic acid | >20% |
| Methanesulfonic acid | >40% |

Example Regarding Process (B)

Example 6

Step B1 was performed according to the examples given in examples 1 to 5.

After filtration of the catalyst the methanolic solution was evaporated in vacuo. The residue was re-dissolved in water and evaporated again to remove remaining methanol. The solution was cooled down. The acid chloride i.e. 2-trifluoromethyl benzoyl chloride, was added at pH 7 to 8. After complete addition of the benzoyl chloride the suspension was stirred for additional 1 h at 20° C. before the addition of solvent (e.g. toluene, xylene, methylcyclohexane, tetrahydrofurane, methyltertbutylether, water). The mixture was heated up to over 85° C. The water phase was then separated and an acid (e.g. aqueous HCl, sulfuric acid, acetic acid) was added to the mixture and stirred for additional 15 minutes. The product precipitates. The cake was washed first with water and then with a solvent before drying under vacuo.

What is claimed is:

1. A process (B) for production of a compound according to formula (I)

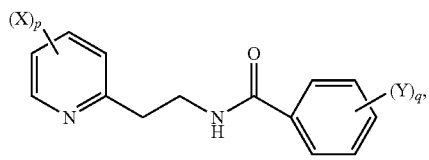

(I)

wherein p is an integer equal to 1, 2, 3 or 4;
each substituent X is, independently of the others, halogen, $C_1$-$C_4$ alkyl or $C_1$-$C_4$ haloalkyl;
q is an integer equal to 1, 2, 3 or 4;
each substituent Y is, independently of the others, halogen, $C_1$-$C_4$ alkyl or $C_1$-$C_4$ haloalkyl;
comprising
in (B1) hydrogenating a substituted 2-methyl cyanopyridyl derivative according to formula (II)

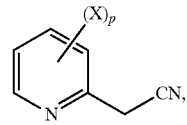

(II)

in the presence of a metal catalyst, a catalyst modifier, and an acid to a substituted 2-ethylaminopyridine derivative according to formula (III) or a corresponding salt thereof,

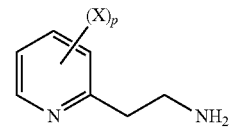

(III)

and
in (B2) reacting a substituted 2-ethylaminopyridine derivative according to the formula (III) as defined in (B1), with a benzoyl halide according to formula (IV)

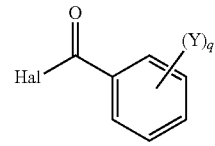

(IV)

wherein
Hal is fluorine, chlorine or bromine;
q is an integer equal to 1, 2, 3 or 4;
each substituent Y is, independently of the others, halogen, $C_1$-$C_4$ alkyl or $C_1$-$C_4$ haloalkyl;
to a compound according to formula (I);
wherein the catalyst is selected from the group consisting of Pd, Pd/C, Pd(OH)₂/C, Pd/Al₂O₃, palladium oxide/C, mixed palladium oxide-hydroxide/C, palladium oxide/Al₂O₃, mixed palladium oxide-hydroxide/Al₂O₃, palladium/SiO₂, palladium oxide/SiO₂, mixed palladium oxide-hydroxide/SiO₂, Pd/CaCO₃, Pd/C-diphenyl-sulfide, Pd/BaSO₄, Pd(II)acetate-polymethylhydrosiloxane, Pd(Fe)/C, Pd/C 5% sulfur, 5% Pd/0.5% V, Pd/Pt, Rh/C, and Pt/C;
wherein the catalyst modifier is selected from the group consisting of n-tetramethylammonium iodide, n-tetraethylammonium iodide, n-tetrabutylammonium iodide, n-tetramethylammonium bromide (TMAB), n-tetraethylammonium bromide, n-tetrabutylammoniumbromide (TBAB), n-tetramethylammonium chloride, n-tetraethylammonium chloride, and n-tetrabutylammoniumchloride; and
wherein the acid is selected from the group consisting of sulfuric acid, HCl, phosphoric acid, and methanesulfonic acid.

2. The process according to claim 1, further comprising in (B3), adding a solvent and an acid to a reaction mixture comprising a precipitated compound according to formula (I).

3. The process according to claim 2, further comprising in (B4), separating an organic phase comprising a compound according to formula (I) from a water phase.

4. The process according to claim 3, comprising
in (B2), adding a base to a reaction mixture.

5. The process according to claim 1
wherein p is 1 or 2;
q is 1;
Y is independently of the others, fluorine, chlorine, or difluoromethyl, trifluoromethyl, dichloromethyl, trichloromethyl; and
the phenyl moiety is substituted by Y in 2- and/or in 6-position;
X is independently of the others, fluorine, chlorine, or difluoromethyl, trifluoromethyl, dichloromethyl, trichloromethyl; and
the 2-pyridyl moiety is substituted by X in 3- and/or in 5-position.

6. The process according to claim 1,
wherein the compound according to formula (I) is (N-[2-[3-chloro-5-(trifluoromethyl)-2-pyridinyl]ethyl]-2-(trifluoromethyl)benzamide).

7. The process according to claim 1,
wherein the catalyst modifier is selected from the group consisting of n-tetramethylammonium bromide (TMAB), n-tetraethylammonium bromide, and n-tetrabutylammonium bromide (TBAB).

8. The process according to claim 1,
wherein each substituent Y is, independently of the others, trifluoromethyl or chlorine.

9. The process according to claim 5,
wherein the phenyl moiety is substituted by Y in the 2-position.

10. The process according to claim 1,
wherein the substituted 2-methyl cyanopyridyl derivative according to formula (II) is 3-chloro-5-(trifluoromethyl)pyridin-2-yl]acetonitrile.

11. The process according to claim 1,
wherein the substituted 2-ethylaminopyridine derivative according to formula (III) is 2-[3-chloro-5-(trifluoromethyl)pyridin-2-yl]ethanamine.

12. The process according to claim 1,
wherein the benzoyl halide according to formula (IV) is 2-trifluoromethyl-benzoyl chloride.

13. The process according to claim 4,
wherein the base is selected from the group consisting of $Na_2CO_3$, $NaHCO_3$, $K_2CO_3$, $KHCO_3$, NaOH, KOH, $Ca(OH)_2$, $Mg(OH)_2$, triethyl amine, and N,N-diisopropylethylamine.

14. The process according to claim 1,
wherein in (B1), said hydrogenating is performed at a temperature in a range from about −20° C. to about 250° C., and
wherein in (B2), said reacting is performed at a temperature in a range from about −20° C. to about 250° C.

15. The process according to claim 1,
wherein in (B1), said hydrogenating is performed at a temperature in a range from about 0° C. to about 150° C., and
wherein in (B2), said reacting is performed at a temperature in a range from about 0° C. to about 150° C.

16. The process according to claim 3,
wherein in (B1), said hydrogenating is performed at a temperature in a range from about −20° C. to about 250° C.,
wherein in (B2), said reacting is performed at a temperature in a range from about −20° C. to about 250° C.,
wherein in (B3), said adding is performed at a temperature in a range from about −20° C. to about 250° C., and
wherein in (B4), said separating is performed at a temperature in a range from about −20° C. to about 250° C.

17. The process according to claim 3,
wherein in (B1), said hydrogenating is performed at a temperature in a range from about 0° C. to about 150° C.,
wherein in (B2), said reacting is performed at a temperature in a range from about 0° C. to about 150° C.,
wherein in (B3), said adding is performed at a temperature in a range from about 0° C. to about 150° C., and
wherein in (B4), said separating is performed at a temperature in a range from about 0° C. to about 150° C.

18. The process according to claim 1, wherein presence of the catalyst modifier results in equal or less than 25% of dehalogenated side products.

19. The process according to claim 1, wherein presence of the catalyst modifier results in equal or less than 10% of dehalogenated side products.

20. The process according to claim 1, wherein presence of the catalyst modifier results in equal or less than 5% of dehalogenated side products.

* * * * *